US008129131B2

(12) United States Patent
Lu et al.

(10) Patent No.: US 8,129,131 B2
(45) Date of Patent: Mar. 6, 2012

(54) PIN1 AS A MARKER FOR ABNORMAL CELL GROWTH

(75) Inventors: Kun Ping Lu, Newton, MA (US); Xiao Zhen Zhou, Newton, MA (US); Gerburg Wulf, Cambridge, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 277 days.

(21) Appl. No.: 12/218,838

(22) Filed: Jul. 18, 2008

(65) Prior Publication Data
US 2009/0258352 A1 Oct. 15, 2009

Related U.S. Application Data

(60) Division of application No. 10/683,880, filed on Oct. 9, 2003, now abandoned, which is a continuation of application No. 09/726,464, filed on Nov. 29, 2000, now abandoned.

(60) Provisional application No. 60/167,800, filed on Nov. 29, 1999, provisional application No. 60/253,676, filed on Nov. 28, 2000.

(51) Int. Cl.
*G01N 33/53* (2006.01)
(52) U.S. Cl. ....................................... 435/7.23
(58) Field of Classification Search .................. None
See application file for complete search history.

(56) References Cited

U.S. PATENT DOCUMENTS

| 5,683,714 A | 11/1997 | Adler-Moore et al. | |
|---|---|---|---|
| 5,952,467 A | 9/1999 | Hunter et al. | |
| 5,972,697 A * | 10/1999 | Hunter et al. | 435/320.1 |

FOREIGN PATENT DOCUMENTS

| WO | WO 97/17986 | 5/1997 |
|---|---|---|
| WO | WO 99/10537 | 3/1999 |
| WO | WO 99/12962 | 3/1999 |
| WO | WO 99/63931 | 12/1999 |
| WO | WO 00/48621 | 8/2000 |

OTHER PUBLICATIONS

Sellers, 1971 Can. Med. Assoc. Journal vol. 105 pp. 836, 839-840 and 842-843.*
U.S. Appl. No. 09/726,464, filed Nov. 29, 2000, Lu et al.
U.S. Appl. No. 10/683,880, filed Oct. 9, 2003, Lu et al.
Crenshaw et al., "The Mitotic Peptidyl-Prolyl Isomerase, Pin1, interacts with Cdc25 and Pix1," *The EMBO Journal* 17(5): 1315-1327 (1998).
Eck and Wilson, "Gene-Based Therapy," In Goodman and Gilman's *The Pharmacological Basis of Therapeutics* 9th ed., New York: McGraw-Hill, pp. 77-101 (1996).
Epstein et al., "Interobserver Reproducibility in the Diagnosis of Prostatic Intraepithelial Neoplasia," *The American Journal of Surgical Pathology* 19(8): 873-886 (1995).
Hunter et al., "Prolyl Isomerases and Nuclear Function," *Cell* 92(2): 141-143 (1998).
Lu et al., "Evidence for a NIMA-Like Mitotic Pathway in Vertebrate Cells," *Cell* 81(3): 413-424 (1995).
Lu et al., "The NIMA Kinase: A Mitotic Regulator in *Aspergillus nidulans* and Vertebrate Cells," *Progress in Cell Cycle Research* 1: 187-205 (1995).
Lu et al., "A Human Peptidyl-Prolyl Isomerase Essential for Regulation of Mitosis," *Nature* 380(6574): 544-547 (1996).
Lu et al., "Function of WW Domains as Phosphoserine- or Phosphothreonine-Binding Modules," *Science* 283(5406): 1325-1328 (1999).
Iadarola et al., "Gene Transfer Approaches to Pain Control," *Molecular Neurobiology of Pain* 9: 337-359 (1997).
Mansour et al., "Key Residues Defining the μ-Opioid Receptor Binding Pocket: A Site-Directed Mutagenesis Study," *Journal of Neurochemistry* 68(1): 344-353 (1997).
McLeod et al., "Selection of Markers to Predict Tumour Response or Survival: Description of a Novel Approach," *European Journal of Cancer* 35(12): 1650-1652 (1999).
Miller and Vile, "Targeted Vectors for Gene Therapy." *FASEB J.* 9(2): 190-199 (1995).
Ranganathan et al., "Structural and Functional Analysis of the Mitotic Rotamase Pin1 Suggests Substrate Recognition is Phosphorylation Dependent," *Cell* 89(6): 875-886 (1997).
Rippmann et al., "Phosphorylation-Dependent Proline Isomerization Catalyzed by Pin1 is Essential for Tumor Cell Survival and Entry into Mitosis," *Cell Growth and Differentiation* 11(7): 409-416 (2000).
Sadee et al., "Constitutive Activation of the μ-Opioid Receptor: A Novel Paradigm of Receptor Regulation in Narcotic Analgesia, Tolerance, and Dependence," *Analgesia* 1(1): 11-14 (1994).
Schutkowski et al., "Role of Phosphorylation in Determining the Backbone Dynamics of the Serine/Threonine-Proline Motif and Pin1 Substrate Recognition," *Biochemistry* 37(16): 5566-5575 (1998).
Shen et al., "The Essential Mitotic Peptidyl-Prolyl Isomerase Pin1 Binds and Regulates Mitosis-Specific Phosphoproteins," *Genes and Development* 12(5): 706-720 (1998).

(Continued)

*Primary Examiner* — Sheela J Huff
(74) *Attorney, Agent, or Firm* — Kristina Bieker-Brady; Clark & Elbing LLP

(57) ABSTRACT

Methods for the use of Pin1 as a marker of abnormal cell growth are disclosed. In one embodiment, the method includes detecting a level of Pin1 to stage an abnormal cell growth, such as breast or prostate cancer. In another embodiment, the method includes evaluating the efficacy of a treatment of an abnormal cell growth, such as cancer, by monitoring the levels of Pin1. In another embodiment, the method includes evaluating the extent of metastasis of abnormal cell growth, such as cancer. The levels of Pin1 can be protein levels or nucleic acid levels.

10 Claims, 6 Drawing Sheets

OTHER PUBLICATIONS

Songyang et al., "Catalytic Specificity of Protein-Tyrosine Kinases is Critical for Selective Signalling," *Nature* 373(6514): 536-539 (1995).

Uchida et al., "Identification and Characterization of a 14 kDa Human Protein as a Novel Parvulin-Like Peptidyl Prolyl *Cis/Trans* Isomerase," *FEBS Letters* 446(2): 278-282 (1999).

Verma and Somia, "Gene Therapy: Promises, Problems and Prospects," *Nature* 389(6648): 239-242 (1997).

Yaffe et al., "Sequence-Specific and Phosphorylation Dependent Proline Isomerization: A Potential Mitotic Regulatory Mechanism," *Science* 278(5345):1957-1960 (1997).

European Search Report for Application No. 00982293.3-1223, dated Mar. 12, 2007.

www.cancer.med.umich.edu/learn/typstage.htm.

* cited by examiner

Clinical and pathological characteristics of breast tissues

| | Normal | Carcinoma | | | |
|---|---|---|---|---|---|
| | | Total | In situ | Grade 2 | Grade 3 |
| Pin1 Positive $\bar{X} \pm SD$ | 0/10†<br>0.114±0.106 | 38/51 (75%)<br>1.072±0.719 | 1/4 (25%)<br>0.564±0.948 | 20/28 (71%)<br>0.924±0.609 | 17/19 (89%)<br>1.399±0.717 |
| Cyclin D1 | 0/10 | 24/51 (47%) | 2/4 (50%) | 10/28 (36%) | 12/19 (63%) |
| HER2/neu | 0/10 | 8/51 (16%) | 0/4 (0%) | 4/28 (14%) | 4/19 (21%) |
| Estrogen receptor | N.D.* | 34/50¶ (68%) | 3/4 (75%) | 20/28 (71%) | 11/18 (61%) |
| Age Median (Range) | 57 (22-91) | 65 (28-90) | 72 (43-80) | 65 (31-90) | 60 (28-78) |

FIGURE 2

Correlation of the Pin1 level with clinical and pathological characteristics

|  |  | Number of cases | Pin1 level ($\bar{X} \pm SD$) | P value |
|---|---|---|---|---|
| Normal |  | 10 | 0.114 ± 0.106 | <0.0001* |
| Tumor |  | 51 | 1.072 ± 0.716 | |
| Tumor Grade | Grade 2 | 28 | 0.924 ± 0.609 | 0.02* |
|  | Grade 3 | 19 | 1.399 ± 0.717 | |
| Cyclin D1† | Positive | 24 | 1.364 ± 0.715 | 0.01* |
|  | Negative | 27 | 0.824 ± 0.631 | |
| HER2/neu† | Positive | 8 | 1.317 ± 0.732 | 0.10 |
|  | Negative | 43 | 1.027 ± 0.713 | |
| Estrogen† Receptor | Positive | 34 | 1.011 ± 0.718 | 0.32 |
|  | Negative | 16 | 1.238 ± 0.720 | |

FIGURE 3

Differentially expressed genes in Pin1-overexpressed MCF-7 cells

| <Up-regulated genes> | <Down-regulated genes> |
|---|---|
| 5-aminolevulinate synthase | Serine/threonine protein kinase sgk |
| CD97 | Alpha 2 actinin |
| BIP/GRP78 | Tu translation elongation factor (p43) |
| PPAR-delta | Platelet-activating factor acetylhydrolase 1b gamma |
| SRY(sex-determining region Y)-box 22 (SOX22) | Eukaryotic translation initiation factor 4E biding protein 1 |
| IFN-inducible gamma 2 protein | |
| Fibronection | |
| Stress inducible phospho protein 1 (STIMP1) | |
| Phosphoenolpyruvate carboxykinase1(PCK1) | |
| C-Myc | |
| Profilin | |
| Unknown NO81 | |
| EST No20-2 | |
| Cyclin D1 | | genes underlined are wnt/beta-catenin/Tcf-4-target gene

FIGURE 4

PIN1 AS A MARKER FOR ABNORMAL CELL GROWTH

RELATED APPLICATIONS

This application is a divisional application of U.S. Ser. No. 10/683,880, filed on Oct. 9, 2003, which is a continuation application of U.S. Ser. No. 09/726,464, filed on Nov. 29, 2000, which is abandoned, which claims priority to U.S. Provisional Ser. No. 60/167,800, filed Nov. 29, 1999, and U.S. Provisional Ser. No. 60/253,676, filed Nov. 28, 2000, each of which is incorporated herein by reference in their entirety. This application is related to International Application PCT/US00/32560, filed Nov. 29, 2000, the entire contents of which are herein incorporated by reference in their entirety.

GOVERNMENT SUPPORT

This invention was made, in whole or in part, by grants R01GM56230 and R01GM58556 from the National Institutes of Health. The Government has certain rights in the invention.

BACKGROUND OF THE INVENTION

The increased number of cancer cases reported in the United States, and, indeed, around the world, is a major concern. Currently there are only a handful of detection and treatment methods available for some specific types of cancer, and these provide no absolute guarantee of success. In order to be most effective, these treatments require not only an early detection of the malignancy, but a reliable assessment of the severity of the malignancy.

Cancers can be viewed as a breakdown in the communication between tumor cells and their environment, including their normal neighboring cells. Growth-stimulatory and growth-inhibitory signals are routinely exchanged between cells within a tissue. Normally, cells do not divide in the absence of stimulatory signals or in the presence of inhibitory signals. In a cancerous or neoplastic state, a cell acquires the ability to "override" these signals and to proliferate under conditions in which a normal cell would not.

In general, cancerous cells must acquire a number of distinct aberrant traits in order to proliferate in an abnormal manner. Reflecting this requirement is the fact that the genomes of certain well-studied tumors carry several different independently altered genes, including activated oncogenes and inactivated tumor suppressor genes. In addition to abnormal cell proliferation, cells must acquire several other traits for tumor progression to occur. For example, early on in tumor progression, cells must evade the host immune system. Further, as tumor mass increases, the tumor must acquire vasculature to supply nourishment and remove metabolic waste. Additionally, cells must acquire an ability to invade adjacent tissue. In many cases cells ultimately acquire the capacity to metastasize to distant sites.

It is apparent that the complex process of tumor development and growth must involve multiple gene products. It is therefore important to define the role of specific genes involved in tumor development and growth and identify those genes and gene products that can serve as targets for the diagnosis, prevention and treatment of cancers.

In the realm of cancer therapy it often happens that a therapeutic agent that is initially effective for a given patient becomes, over time, ineffective or less effective for that patient. The very same therapeutic agent may continue to be effective over a long period of time for a different patient. Further, a therapeutic agent that is effective, at least initially, for some patients can be completely ineffective or even harmful for other patients. Accordingly, it would be useful to identify genes and/or gene products that represent prognostic genes with respect to a given therapeutic agent or class of therapeutic agents. It then may be possible to determine which patients will benefit from particular therapeutic regimen and, importantly, determine when, if ever, the therapeutic regime begins to lose its effectiveness for a given patient. The ability to make such predictions would make it possible to discontinue a therapeutic regime that has lost its effectiveness well before its loss of effectiveness becomes apparent by conventional measures.

SUMMARY OF THE INVENTION

The invention relates to methods of detecting abnormal cell growth in a mammal, comprising assessing the level of Pin1 in a test sample from the mammal, wherein an elevation in the levels of Pin-1 is indicative of abnormal cell growth. In one embodiment, the level of Pin-1 is a protein level. In another embodiment, the level of Pin1 is a nucleic acid level.

Specifically, the invention relates to epithelial test samples such as breast or prostate epithelial test samples. In another embodiment, the test sample can be a body fluid sample, such as blood, ascites or brain fluid.

In particular, the invention relates to a method of detecting abnormal cell growth in a mammal, comprising the steps of detecting a level of Pin1 in a test sample and comparing the level of Pin1 in the test sample with a control level, wherein a difference in the level of Pin-1 in the test sample is indicative of abnormal cell growth in the mammal. An elevation in the level of Pin1 compared to the control level is indicative of the presence the abnormal cell growth in the mammal. Methods of the invention can detect abnormal cell growth that is benign or malignant (e.g., breast, ovarian, skin, prostatic, cervical, digestive track, liver, lung, kidney or testicular abnormal cell growth).

The invention further relates to a method of detecting abnormal cell growth in a mammal by assessing the level of Pin1 protein in a test sample from the mammal, comprising the steps of contacting the test sample with an antibody having specificity for Pin1 under conditions suitable for binding of the antibody to Pin1 thereby resulting in the formation of a complex between the antibody and Pin1; detecting the complex between the antibody and Pin1; and comparing the amount of the complex in the test sample with an amount of a complex in a control sample, wherein an elevation in the amount of the complex between the antibody and Pin1 in the test sample compared to the complex in the control sample is indicative of abnormal cell growth. The antibody can be a polyclonal or a monoclonal antibody and, optionally, detectably labeled. (e.g., radioactive, enzymatic, biotinylated and/or fluorescence).

The invention also relates to a method of detecting abnormal cell growth in a mammal, comprising the steps of detecting a level of Pin1 nucleic acid in a test sample; and comparing the level of Pin1 in the test sample with a level of Pin1 in a control sample is indicative of abnormal cell growth.

Another embodiment of the invention relates to a method of determining abnormal cell growth in a mammal, comprising the steps of contacting a test sample obtained from the mammal with a nucleic acid probe to a Pin1 nucleic acid; maintaining the test sample and the nucleic acid probe under conditions suitable for a hybridization; detecting the hybridization between the test sample and the nucleic acid probe;

and comparing the hybridization in the test sample from the mammal to a control test sample without abnormal cell growth, wherein an elevation in the hybridization signal in the test sample from the mammal compared to the control sample is indicative of abnormal cell growth. The nucleic acid probe can be optionally labeled with a label comprising a fluorescent, radioactive, and enzymatic label.

In yet another embodiment, the invention relates to a method of determining a stage of abnormal cell growth, comprising assessing a level of Pin1 in a test sample from a mammal. Specifically encompassed by the invention, is a method of staging breast or prostate cancer abnormal cell growth.

The invention also relates to a method of determining a stage of abnormal cell growth in a mammal by assessing the level of Pin1 in a test sample from the mammal, comprising the steps of contacting the test sample with an antibody having specificity for Pin1 under conditions suitable for binding of the antibody to Pin1 thereby resulting in the formation of a complex between the antibody and Pin1; and comparing the amount of the complex in the test sample with an amount of a complex in a control sample, wherein an elevation in the amount of the complex in the test sample compared to the control sample is indicative of the stage of the cancer.

Another aspect of the invention is a method of determining a stage of an abnormal cell growth in a mammal, comprising assessing a level of a Pin-1 nucleic acid in a test sample, comprising the steps of performing a polymerase chain reaction with oligonucleotide primers capable of amplifying the Pin1 nucleic acid; detecting a level of amplified nucleic acid fragments of the Pin1 nucleic acid; and comparing the level of amplified nucleic acid fragments in the test sample to a sample comprising varying stages of the abnormal cell growth, wherein the stage of the abnormal cell growth in the mammal is determined.

The invention also relates to a method of determining a stage of abnormal cell growth in a mammal, comprising the steps of contacting a test sample obtained from the mammal with a nucleic acid probe to a Pin1 nucleic acid; maintaining the test sample and the nucleic acid probe under conditions suitable for hybridization; detecting the hybridization between the test sample and the nucleic acid probe; and comparing the hybridization in the test sample from the mammal to a sample comprising varying stages of the cancer, wherein the stage of abnormal cell growth in the mammal is determined.

In still another embodiment, the invention relates to a method of evaluating the efficacy of a treatment (e.g., surgery, radiation, chemotherapy) of abnormal cell growth in a mammal, comprising comparing a level of Pin1 in at least two test samples comprising a first test sample obtained at a first time and a second test sample obtained at a later second time, wherein a decrease in the level of Pin1 between the two test samples indicates the efficacy of the treatment of the abnormal cell growth in the mammal.

The invention also relates to a method of evaluating the extent of metastasis of abnormal cell growth in a mammal comprising assessing the level of Pin1 in a test sample from the mammal.

In another embodiment, the invention relates to a kit for detecting an abnormal cell growth in a mammal comprising one or more reagents for detecting a level of Pin1 in a test sample obtained from the mammal. Specifically encompassed by the invention are kits for detecting breast or prostate cancer employing protein or nucleic acid test samples. In particular, kits for Western blotting, immunocytochemistry, radioimmunoassays (RIA) and enzyme linked immunoabsorption assays are kits of the invention. Also included in the invention are kits, wherein the one or more reagents for detecting the abnormal cell growth are used for carrying out a nucleic acid amplification reaction, such as a polymerase chain reaction based assay.

In yet another embodiment, the invention relates to a kit for determining a stage of abnormal cell growth in a mammal comprising one or more reagents for detecting a level of Pin1 in a test sample obtained from the mammal. Specifically encompassed by the invention are kits for staging of abnormal cell growth of breast or prostate cancer.

Also included in the invention are kits for evaluating the efficacy of a cancer treatment in a mammal, comprising one or more reagents for detecting a level of Pin-1 in a test sample obtained from the mammal.

The invention described herein provides methods of detecting abnormal cell growth such as a breast cancer or prostate cancer tumor. Advantages of the claimed invention include, for example, the rapid and sensitive nature of detection in a cost effective manner. The methods of the invention can readily detect various stages of aggressive and/or metastasis of abnormal cell growth such as breast or prostate cancer, thereby indicating an appropriate treatment method the progress of which can be monitored by the methods described in the invention.

The invention also provides a method for facilitating the diagnosis of a state associated with abnormal cell growth in a subject, comprising detecting the level of a Pin1 marker in a sample from the subject as an indication of whether the subject has a state associated with abnormal cell growth, thereby facilitating the diagnosis of the subject. The invention further provides a method for facilitating the diagnosis of cancer in a subject, comprising detecting the level of a Pin1 marker in a sample from the subject as an indication of whether the subject has cancer, thereby facilitating the diagnosis of the subject. In related embodiments, the subject is receiving, or has received, therapy for a state associated with abnormal cell growth and the diagnosis is used to evaluate the subject's response to the therapy. In yet another related embodiment, the subject is involved in a therapy agent clinical trial and the diagnosis is used to evaluate the effectiveness of an agent of the clinical trial.

Another aspect of the invention provides a method of treating a subject for a state associated with abnormal cell growth, comprising administering a Pin1 modulator to the subject such that the state associated with abnormal cell growth is treated. The invention further provides a method of treating a subject for cancer, comprising administering a Pin1 modulator to the subject such that the cancer is treated.

The invention described herein provides a packaged kit for carrying out a method of the invention, wherein the kit comprises at least one reagent for assaying levels of Pin1 in a sample from a subject, and instructions for using the at least one reagent to assay levels of Pin1 in a sample from a subject for the described method. The invention described herein further provides packaged kit for carrying out a method of the invention, wherein the kit comprises at least one Pin1 modulator, and instructions for using the Pin1 modulator in the described method.

DESCRIPTION OF THE FIGURES

FIG. 2 depicts a statistical comparison of the quantified levels of Pin1 and other markers in normal and cancerous breast tissues. Pin1 levels are considered positive in this study if the Pin1/actin ration is higher than mean plus three times standard deviation ($X_{mean} \pm 3SD$) of normal controls. The presence of CyclinD1 and HER2/neu were determined by immunoblotting. Estrogen receptor was defined as positive if its levels were >10 fmol/l, as determined by RIA. (=number of cases examined, *=estrogen receptors in controls not determined, ¶=estrogen receptor determination for one patient not available).

FIG. 3 depicts the significance of the differences in Pin1 levels between various clinical and pathological categories as analyzed by the Kruskall-Wallace Test. (=analysis done only in tumors; * differences are statistically significant when $P \leq 0.05$ and highly significant when $P \leq 0.01$.

FIG. 4 depicts a number of genes whose expression is modulated (up- or down-regulation) by Pin1 overexpression in breast cancer cells.

Figure 1:
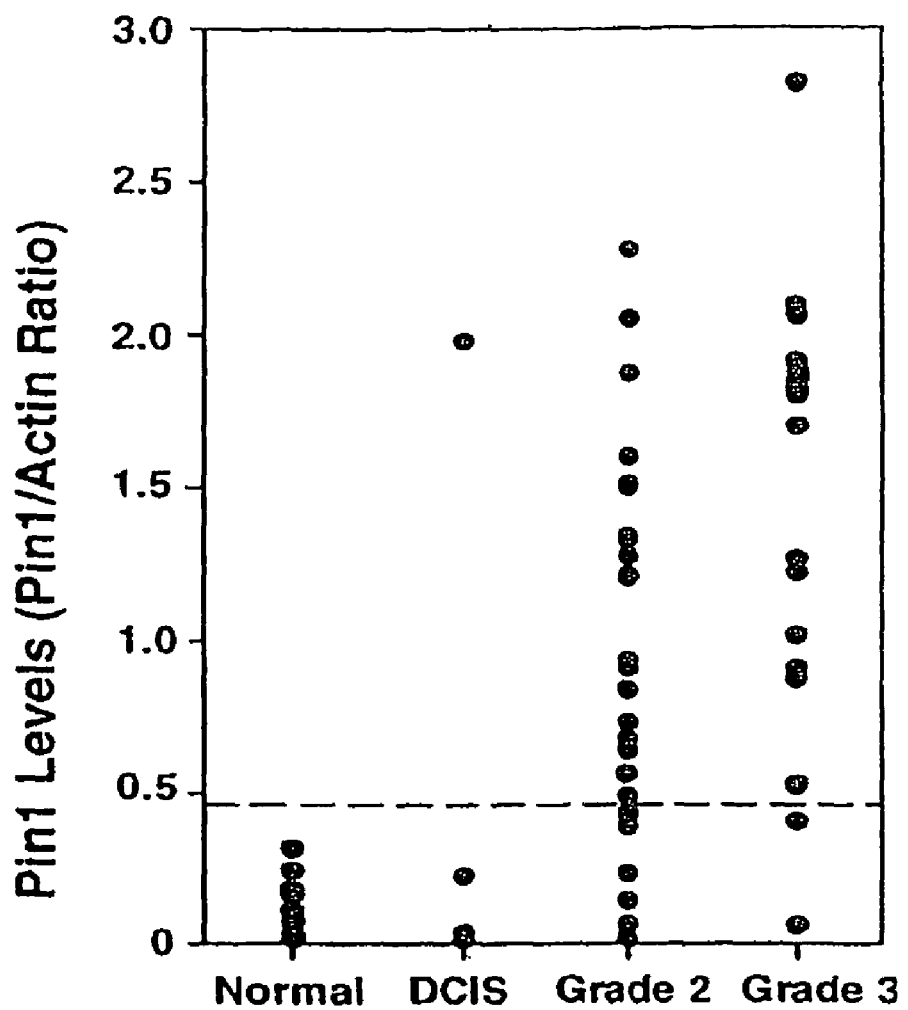
FIG. 1 depicts an assay of Pin1 protein levels in 10 normal (non-cancerous) breast tissues and various stages of 51 breast cancer samples. Expression of actin was used to normalize values, and Pin1 levels are compared as Pin1/actin ratios. "DCIS" indicates "ductal carcinoma in situ".

Panel "a" shows a cotransfection experiment whereby Pin1 and Ha-Ras cooperate to increase the activity of c-Jun as a function of increasing amounts of transfected Pin1. In this experiment, HeLa cells were cotransfected with vector, c-Jun or c-Jun+H-Ras, and different amounts of Pin1 expression vector for 24 hr and then subjected to the luciferase assay. The −964 cyclin D1-luciferase was used promoter as a reporter gene.

Panel "b" shows increasing or diminishing c-Jun activity by up- or down-regulation of Pin1. HeLa cells were cotransfected with different constructs, as indicated, and then subjected to the luciferase assay. Note, two different concentrations of Pin1$^{AS}$ DNA (0.1 and 0.5 μg) were used, with a stronger inhibitory effect when more DNA was used.

Panel "c" shows abrogation of the ability of Pin1 to increase the c-Jun activity by mutation of the phosphorylation sites of c-jun (S63/73). Cells were co-transfected with Pin1, Ha-Ras, various amounts of c-Jun or c-Jun mutant S63/73A construct, as well as the −964 cyclin D1 luciferase reporter gene and then subjected to the luciferase assay.

Panel "d" shows inhibition of the ability of Pin1 to increase the c-Jun activity by dominant-negative Ras (DN-Ras). Cells were co-transfected with c-Jun or c-Jun+Pin1 and increasing amounts of DN-Ras, as well as the −964 cyclin D1 luciferase reporter gene, and then subjected to the luciferase assay.

Panel "e" shows abrogation of the ability of Pin1 to enhance c-Jun activity by inactivating (mutating) the Pin1 PPIase activity. Cells transfected with −964 cyclin D1 luciferase reporter gene were co-transfected with control vector, c-Jun, or c-Jun+Ha-Ras and Pin1 or its PPIase-negative mutant Pin1$^{R68,69A}$ and then subjected to a luciferase assay. Pin1$^{R68,69A}$ fails to isomerize phosphorylated S/T-P bonds.

Panel "f" shows abrogation of the ability of Pin1 to increase the c-Jun activity by inactivating (mutating) the Pin1 phosphoprotein-binding activity. Cells transfected with −964 cyclin D1 luciferase reporter gene were co-transfected with vectors, c-Jun, or c-Jun+Ha-Ras and GFP-Pin1 or one of its WW domain mutants GFP-Pin1$^{W34A}$ or GFP-Pin1$^{S16E}$, then subjected to luciferase assay. Neither GFP-Pin1$^{W34A}$ nor GFP-Pin1$^{S16E}$ could bind phosphoproteins (data not shown). Note, GFP fusion proteins were used because these WW domain Pin1 mutants were not stable in cells, but when expressed as GFP fusion proteins, they were stable, although at reduced levels (data not shown). Although the absolute maximal luciferase activity was not as high as other experiments, which is likely due to lower levels of GFP fusion proteins being expressed, the overall trends were same.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to the discovery that the levels of Pin1 are elevated in cells undergoing abnormal cell growth. The invention further relates to the discovery that the levels of Pin1 increase as a collection of cells undergoing abnormal cell growth, e.g., a tumor, become more aggressive, proliferative or metastasize. Thus, elevated levels of Pin1 are indicative of a tumor and are used as a tumor marker.

The events during mitosis are some of the most dramatic in biology as well as most attractive targets for drug development. Many of the mitotic events are tightly regulated by protein phosphorylation on serine or threonine residues preceding proline. Proline is important for determining protein structure because it exists in cis or trans conformation and can put kinks into a polypeptide chain. Although phosphorylation has been proposed to regulate the function of a protein, via a conformational change, little was known what phosphate additions actually do and how phosphorylation is converted into a programmed set of the mitotic events until the discovery of the Pin1 subfamily of proteins.

Phosphorylation on serine/threonine-proline motifs restrains cis/trans prolyl isomerization, and also creates a binding site for the essential protein Pin1. Pin1 binds and regulates the activity of a defined subset of phosphoproteins, as well as participating in the timing of mitotic progression. Both structural and functional analyses have indicated that Pin1 contains a phosphoserine/threonine-binding module that binds phosphoproteins, and a catalytic activity that specifically isomerizes the phosphorylated phosphoserine/threonine-proline. Both of these Pin1 activities are essential for Pin1 to carry out its function in vivo.

Pin1 is dramatically overexpressed in human cancer samples and the levels of Pin1 are correlated with the aggressiveness of tumors. Furthermore, we have found that a potent anticancer reagent with an unknown mechanism potently and reversibly inhibits Pin1 isomerase activity. Moreover, inhibition of Pin1 by various approaches, including the Pin1 inhibitor, Pin1 antisense polynucleotides, or genetic depletion, kills human and yeast dividing cells by inducing premature mitotic entry and apoptosis. Thus, upon phosphorylation, Pin1 latches onto phosphoproteins and twists the peptide bond next to the proline, which regulates the function of phosphoproteins and participates in controlling the timing of mitotic progression. This new regulatory mechanism not only will help the cell orchestrate the organized set of the mitotic events, but also is a novel and attractive target for drug development. Our studies also indicate that detection of Pin1 protein levels may be a novel universal tumor marker for identifying tumor cells and monitoring their aggressiveness and their response to cancer treatment, such as surgical, drug (e.g., chemotherapeutics) or radiation treatment.

In order to reproduce and multiply, every cell must execute an orderly series of events, called the cell cycle, which usually contains four phases, GI (gap 1), S (DNA synthesis), G2 (gap 2) and M (mitosis). The events during mitosis are some of the most dramatic in biology. The chromosomes condense, the nuclear membrane disappears, the mitotic spindle assembles and eventually chromosomes are pulled apart to the opposite poles of the dividing cell. Many of these events are regulated by phosphorylation of proteins on serine or threonine residues immediately preceding proline (Ser/Thr-Pro) due to activation of cyclin-dependent protein kinase Cdc2 at entry into mitosis. Cdc2 is highly conserved during evolution and considerable progress has been made in the understanding of its upstream regulators (Nurse (1994) *Cell* 79:547-550; King et al. (1994) *Cell* 79:563-571; Lu and Hunter (1995) *Progress in Cell Cycle Research* 1: 187-205). Activation and inactivation of the cyclin B/CDC2 complex, frequently referred to as the mitosis-promoting factor, have been shown to be critical for entry into and exit from mitosis, respectively, in all eukaryotic cells so far examined. At the G2/M transition, activation of Cdc2 requires multiple events; these include the synthesis and binding of cyclin B, constitutive phosphorylation of Cdc2 on an activating site by CAK, and finally, Cdc25-dependent dephosphorylation of inactivating sites that have been phosphorylated by Wee1 and Myt1 (Nurse (1994) *Cell* 79:547-550; King et al. (1994) *Cell* 79:563-571). Irreversible inactivation of Cdc2 at the metaphase/anaphase boundary requires the ubiquitin dependent proteolysis of its cyclin subunit. However, how activation of Cdc2 elicits a series of mitotic events is less well understood.

Like other cyclin-dependent protein kinases (Cdks), Cdc2 belongs to a subfamily of proline-directed protein kinases that phosphorylate proteins on Ser/Thr-Pro sites (Nigg (1995) *BioEssays* 17:471-480). At the G2/M transition, abrupt activation of Cdc2 leads to the phosphorylation of a large number of proteins. These phosphoproteins are localized in various mitotic structures (Nigg (1995) *BioEssays* 17:471-480) and most of them are the MPM-2 monoclonal antibody, which was originally generated using total mitotic extracts from HeLa cells as antigens (Davis et al. (1983) *Proc Natl Acad Sci USA* 80:2926-2930). MPM-2 appears to recognize conserved phosphoepitopes that contain the phosphorylated Ser/Thr-Pro motif on at least 50 mitosis-specific phosphoproteins. This remarkable and puzzling specificity of MPM-2 for a defined subset of phosphoproteins has been seen in all eukaryotic organisms so far examined. The MPM-2 antigens include many proteins that play an important role in mitosis, such as NIMA, Myt1, Wee1, Cdc25, topoisomerase IIa, tau, Map 4, INCENP and Cdc27 (Stukenberg et al. (1997) *Curr Biol* 7:338-48). Interestingly, MPM-2 does not recognize many proteins that are also phosphorylated on Ser/ThrPro sequences during interphase, these results suggest common phosphorylated epitopes present in phosphoproteins. However, it has remained unclear what role these phosphoepitopes play during mitotic progression, why such epitopes are highly conserved during evolution and what their endogenous ligand (s) is.

Serine/threonine phosphorylation has been thought to regulate the function of proteins through conformation changes and thereby trigger an organized and programmed set of structural modifications that occur during mitosis. In fact, phosphorylation of certain proteins has been actually shown to regulate specific mitotic events. For example, phosphorylation of nuclear lamin A, small GTP-binding proteins Rab1A and Rab4B, and the kinesin-related motor Eg5 by Cdc2 has been shown to play an essential role in regulating nuclear lamina disassembly, intracellular membrane transport and bipolar spindle formation during mitosis, respectively (Heald and McKeon (1990) *Cell* 61:579-89; Bailly et al. (1991) *Nature* 350:715-8; Blangy et al. (1995) *Cell* 83:1159-69). However, it is not clear what the phosphorylation on the Ser/Thr-Pro motif actually does and how these abrupt changes in the phosphorylation state at the G2/M transition lead to an organized and programmed set of the mitotic events.

By searching for proteins that physically interact and functionally suppress the kinase NIMA, one of such MPM-2 antigens, we have recently isolated a novel protein, Pin1 (Lu et al. (1996) *Nature* 380:544-547). Pin1 is highly conserved and contains a protein-interacting module, called WW domain, and a catalytically active peptidyl-prolyl isomerase (PPIase). Pin1 is structurally and functionally distinct from members of two other well-characterized families of PPIases, the cyclophilins and the FKBPs (Lu et al. (1996) *Nature* 380:544-7). PPIases are ubiquitous enzymes that catalyze the typically slow prolyl isomerization of proteins, allowing relaxation of local energetically unfavorable conformational states (Hunter (1998) *Cell* 92:141-143). Interestingly, phosphorylation on Ser/Thr residues immediately preceding Pro not only alters the prolyl isomerization rate (Schutkowski et al. (1998) *Biochemistry* 3 7:5566-75), but also creates a binding site for the WW domain of Pin1 (Yaffe et al (1997) *Science* 278:1957-1960; Shen et al. (1998) *Genes Dev.* 12:706-720). The WW domain acts a novel phosphoserine-binding module targeting Pin1 to a highly conserved subset of phosphoproteins (Lu et al. (1998) *Science* 283:1325-1328). Furthermore, Pin1 displays a unique phosphorylation-dependent PPIase that specifically isomerizes phosphorylated Ser/Thr-Pro bonds and regulates the function of phosphoproteins (Yaffe et al (1997) *Science* 278:1957-1960; Shen et al. (1998) *Genes Dev.* 12:706-720). These results suggest a novel signaling regulatory mechanism: the isomerase Pin1 binds proteins that have been phosphorylated by Pro-directed kinases, and induces a conformational change to regulate their function. Pin1 could provide a new post-translational level of control to allow the general increase in protein phosphorylation to result in the organized and programmed set of mitotic events.

Taken together, these results indicate that the Pin-1 subfamily of enzymes is a novel diagnostic and therapeutic target for diseases characterized by uncontrolled cell proliferation, primarily malignancies.

Pin1 is a Conserved PPIase Essential for Mitosis

Pin1 encodes 163 amino acid residues that are arranged in two identifiable domains, an N-terminal WW domain and a C-terminal peptidyl-prolyl isomerases (PPIases, rotamase) domain (Lu et al. (1996) *Nature* 380:544-7). PPIases are ubiquitous enzymes catalyzing the otherwise slow reaction, namely the cis/trans isomerization of the peptide bond on the N-terminal side of proline residues in proteins (Hunter (1998) *Cell* 92:141-143). There are two families of conventional PPIases, cyclophilins (Cyps) and FK506 binding proteins (FKBPs) and a recently identified third family of PPIases with the phototype being bacterial parvulin. These three PPIase families are unrelated in their primary sequences.

The proposed roles for PPIases involve the catalysis of protein folding or the trafficking of newly assembled proteins (Hunter (1998) *Cell* 92:141-143). Due to the unique five carbonyl-ring, proline residues introduce a backbone switch into the polypeptide chain. Although cis/trans isomerization about the prolyl bond occurs spontaneously, acceleration of this process by PPIases could play a role in protein folding or refolding by catalyzing a rate-liming step (Hunter (1998) *Cell* 92:141-143). The original finding that the in vitro folding of ribonuclease A involves a mixture of slow and fast folding species differing in the isomeric state of prolyl peptide bonds prompted the hypothesis that catalysis of this isomerization would represent a general mechanism for accelerating protein folding in vivo. Out of various functions shown for PPIases, the most well-characterized function of the cyclophilins and FKBPs is their role in the immune system, because of their importance as cellular receptors for the clinically relevant immunosuppressive drugs (Schreiber (1991) *Science* 251:283-7; Hunter (1998) *Cell* 92:141-143). When the cyclophilins and FKBPs bind the immunosuppressive drugs cyclosporin A and FK506, respectively, there are two common outcomes: inhibition of the PPIase activity and inhibition of the common target calcineurin.

The inhibition of the calcineurin phosphatase activity that prevents lymphocytes from responding to antigen-induced mitogenic signals, thus resulting in the immunosuppression. However, the inhibition of the PPIase activity apparently is unrelated to the immunosuppressive property of the drug/PPIase complexes (Schreiber, 1991; Hunter (1998) *Cell* 92:141-143). Even more surprisingly, deletion of all conventional PPIases, 8 cyclophilins and 4 FKBP, in same cells does not have any significant phenotype (Dolinski et al. (1997) *Proc. Natl. Acad. Sci. USA* 94:13093-131098). Therefore, evidence for the biological importance of PPIase activity has been elusive.

In contrast, Pin1 is the first PPIase gene that is essential for cell survival. Pin1 is 45% identical to Ess1p/Ptf1p, an essential protein in budding yeast, and functionally complemented the essI-null mutation (Lu et al. (1996) *Nature* 380:544-7). These results have demonstrated that Pin1 is structurally and functionally homologous to Ess1p/Ptf1p (Hanes et al. (1989) *Yeast* 5:55-72; Hani et al. (1995) *Febs Lett* 365:198-202). Subsequently, Pin1 homologous genes and Pin1-like genes (Pin1-Ls) have been identified in all eukaryotic cells so far examined, including mammals, *Xenopus, Drosophila, Dictyostelium*, budding and fission yeast as well as *Aspergillus nidulans* (Lu et al. (1996) *Nature* 380:544-7; Hanes et al., 1989; Maleszka et al. (1996) *Proc Natl Acad Sci USA* 93:447-51; Shen et al. (1998) *Genes Dev.* 12:706-720; Kops et al. (1998) *J. Biol. Chem.* 273:31971-6), sequences deposited in GenBank). In addition, the *Drosophila* Pin1 homologue Dodo also functionally rescues the Ess1/Ptf1 deletion mutation in yeast. These results indicate that Pin1 protein is highly conserved during evolution.

The sequence alignment analysis also indicate that in contrast to bacterial and human parvulins, the phototype of this new family of PPIases, Pin1 and Pin1-like genes (Pin1-Ls), including apple Pin1-L1 (K. P. Lu et al., unpublished data), have a unique feature in the active site. They contain two highly conserved two positively charged Arg residues, which we have now shown to confer the phosphorylation-specific prolyl isomerase activity (Yaffe et al (1997) *Science* 278:1957-1960), as described below. These results indicate that Pin1 and Pin1-Ls belong to a distinct subfamily of PPIases.

To determine the function of Pin1 and its homologues during the cell cycle, we have constructed a haploid yeast strain that has the endogenous Ess1/Ptf1 deleted, but expresses human Pin1 under control of the inducible GALL promoter. By manipulating expression of Pin1, we demonstrated that depletion of Pin1 from yeast induced mitotic arrest and subsequent nuclear fragmentation, without affecting DNA synthesis (Lu et al. (1996) *Nature* 380:544-7). Significantly, a similar phenotype was also observed in HeLa cells upon expression of an antisense Pin1 construct (Lu et al. (1996) *Nature* 380:544-7). Conversely, overexpression of Pin1 prevented entry into mitosis in HeLa cells and *Xenopus* extracts (Lu et al. (1996) *Nature* 380:5447; Shen et al., 1998; Crenshaw et al. (1998)*EMBO J.* 17:1315-27). These results have demonstrated that Pin1 is the first PPIase that is essential for cell survival, specifically required for proper progression of mitosis.

Pin1 is a Phosphorylation-Specific Prolyl Isomerase

Phosphorylation of Ser/Thr-Pro motifs is particularly relevant for cell cycle control since the known specificity of the CDKs, including CDC2, is for Ser/Thr-Pro in a variety of CDK targets (Nigg (1995) *BioEssays* 17:471-480). Proline residues provide a potential backbone switch in the polypeptide chain, which can be controlled by the cis/trans isomerization about the peptidyl-prolyl bond (Hunter (1998) *Cell* 92:141-143). Although phosphorylation on Ser/Thr has been proposed to alter the conformation of a protein, few clues are known about what the conformational changes actually are and little was known whether phosphorylation regulates the conformation of the Ser/Thr-Pro bonds. To address this question, a series of peptides that contain the phosphorylated or unphosphorylated Ser/Thr-Pro motif were synthesized, and their conformations were characterized (Schutkowski et al., 1998).

Phosphorylation on Ser/Thr-Pro, but not Tyr-Pro significantly altered the rate of the cis to trans isomerization, when compared with the unphosphorylated analogues. Furthermore, studies of the pH dependence of the isomerization of the phosphopeptides have revealed that the cis/trans isomerization rate was most affected when the phosphate of pThr was in the dianionic state (Schutkowski et al. (1998) *Biochemistry* 3 7:5566-5575). These effects of phosphorylation on isomerization were specific for phosphorylated Ser/Thr since neither phosphorylated Tyr nor glutamic acid affected the prolyl isomerization (Schutkowski et al. (1998) *Biochemistry* 3 7:5566-5575). Thus, these results have demonstrated that protein phosphorylation specifically changes the isomerization rate of the Ser/Thr-Pro peptide bonds.

Since phosphorylation on the Ser/Thr-Pro motif alters the cis/trans isomerization rate, an enzyme would be needed to catalyze this reaction. However, when members of the cyclophilins and FKBPs were tested on a series of chromogenic oligopeptide substrates. Surprisingly, neither Cyp 18 nor FKBP 12 was able to effectively catalyze isomerization of peptides with pSer/Thr-Pro moieties, as compared to peptides lacking phosphate (Table 1). In contrast, Tyr-Pro bonds were acceptable substrates for both enzymes no matter in the phosphorylated or nonphosphorylated from. These results have demonstrated that phosphorylation on the Ser/Thr-Pro motif renders the prolyl-peptidyl bond resistant to the catalytic action of conventional PPIases, and also suggested the need for a different enzyme to catalyze this reaction.

In the light of the putative substrate specificity revealed by the X-ray structure of Pin1 mentioned above, Pin1 is a PPIase that can isomerize the phosphorylated Ser-Pro peptide bonds. As expected, Pin1 displays the unique substrate specificity. Pin1 had a relatively low level of isomerization activity with peptides containing an Ala-Pro peptide bond (Yaffe et al (1997) *Science* 278:1957-1960), despite relatively ordered binding of an Ala-Pro dipeptide in the Pin1 crystal structure (Ranganathan et al. (1997) *Cell* 89:875-886). Incorporating negatively charged side chains of Glu and Asp immediately preceding the Pro residue, which could mimic the pSer, resulted in significant increases in isomerization activity. Unlike Cyp1 18 and FKBP12, peptides containing a Tyr residue preceding the Pro proved to be extremely poor substrates for Pin1, and no increase in activity was observed when Tyr was phosphorylated (Table 1). The most strikingly feature of Pin1 is that its isomerase activity is highly specific for peptide with pSer/Th-r-Pro bonds. As shown in Table 1, Pin1 displayed very low levels of isomerase activity for substrates containing Ser-Pro or Thr-Pro bonds.

Phosphorylation of these peptides on Ser or Thr residues dramatically increased the $k_{cat}/K_m$ values about 300-fold. With the best available substrate identified thus far, the specificity constant of Pin1 PPIase activity was increased up to 1300 fold, as compared to its nonphosphorylated counterpart (Yaffe et al (1997) *Science* 278:1957-1960), indicating that Pin1 is a sequence and phosphorylation-specific PPIase. These findings have demonstrated the dramatic differences in substrate specificity between Pin1 and the conventional PPIases of the cyclophilin and FKBP families.

These differences in isomerase activity result from different organization of the Xaa-Pro binding pocket. In all PPIases, a hydrophobic pocket containing aromatic and aliphatic residues sequesters the aliphatic Pro side chain (Ranganathan et al. (1997) *Cell* 89:875-886). Therefore, the residues responsible for determining substrate preference must reside at the entrance to the Pro-binding pocket. In Pin1 and its homologues, a cluster of basic residues at this site is formed by the side chains of conserved residues Arg68 and Arg69. To determine the importance of this basic cluster for the unique Pin1 substrate specificity, site-specific mutations have been introduced into the active site of Pin1. Substitution of both Arg-68 and -69 by Ala residues reduced the kcat/Km over 500-fold compared to wild type Pin1 for the phosphorylated substrate, approaching the values obtained with the nonphosphorylated peptide (Yaffe et al (1997) *Science* 278:1957-1960). The catalytic activity of $Pin1^{R68,69A}$ was the same as wild-type Pin1 when the nonphosphorylated peptide was used as a substrate, suggesting that these mutations did not grossly affect the structure of Pin1.

These data strongly argue that this cluster of basic residues is involved in coordinating the phosphate of pSer/Thr (Yaffe et al (1997) *Science* 278:1957-1960). This idea has been confirmed by our recent finding that apple Pin1-L1. which does not have a WW domain, but contain the two invariant Arg residues in the active site, also displayed pSer/Thr-Pro-specific PPIase activity (Lu, et al., unpublished data). Conspicuously, bacterial and human parvulins, the prototype member of this new family of PPIases, were unable to catalyze the cis/trans isomerization of phosphorylated Ser/Thr-Pro bonds and instead preferred the Arg-Pro bond (Yaffe et al (1997) *Science* 278:1957-1960; Rahfeld et al. (1994) *FEBS Lett.* 343:65-69; Uchida et al. (1999) *FEBS Lett.* 446:278-82). Interestingly, the preference is explained by the fact that the two Arg residues of the basic cluster are replaced by two Glu residues (Rahfeld et al. (1994) *FEBS Lett.* 343:65-69; Uchida et al. (1999) *FEBS Lett.* 446:278-82). Likewise, in FKBP 12, two Ile residues (190 and 191) occupy the same spatial positions as Arg68 and Arg69 in Pin1, rationalizing FKBP's preference for hydrophobic residues preceding the Pro in contrast to polar or acidic/phosphorylated amino acids. These studies have demonstrated that the phosphorylation-specific substrate specificity of Pin1 and Pin1-like proteins is originated in their unique structural features in the active sites.

Pin1 Targets a Defined Subset of Phosphoproteins.

The above results indicate that Pin1 is a unique PPIase specific for the pSer/Thr-Pro bonds in vitro and is specifically required for proper progression during mitosis in vivo. What is the basis for the cell cycle specificity of the Pin1 function? As an attempt to answer these questions, we determined Pin1 levels and Pin1-binding activity at different phases of the cell cycle (Shen et al. (1998) *Genes Dev.* 12:706-720). Although Pin1 levels were constant through the cell cycle, Pin1 directly bound a number of proteins in a cell cycle-regulated manner, as shown by Pin1 "far western" analysis (Shen et al. (1998) *Genes Dev.* 12:706-720). Pin1 binding activity was low during GI and S, increased in G2/M and was highest when cells were arrested in M. Since the crystal structure predicted that Pin1 could interact with a pSer/Thr-Pro motif which is recognized by the MPM-2 antibody on phosphoproteins, we asked if Pin1I interacted with MPM-2 antigens (Shen et al. (1998) *Genes Dev.* 12:706-720).

GST and GST-Pin1 beads were added to interphase or mitotic extracts, followed by analysis of MPM-2 antigens present in the beads. Pin1 bound and precipitated almost all of the MPM-2 antigens in a HeLa mitotic extract. To determine if endogenous Pin1 interacts with MPM-2 antigens, Pin1 was immunoprecipitated from either interphase or mitotic HeLa extracts and the Pin1 interacting proteins were probed with MPM-2. MPM-2 antigens were co-immunoprecipitated with anti-Pin1 antibodies in a mitosis-specific manner, indicating that a stable complex between MPM-2 antigens and Pin1 exists in the cell.

The Ser/Thr-Pro motif is the target for phosphorylation by a range of protein kinases including Cdc2 and MAP kinases, and is present in a large number of kinase substrates (2). However, since Pin1 only binds a defined subset of phosphoproteins, additional factors must determine whether or not a phosphorylated protein is a target for Pin1 regulation. Further experiments using oriented degenerate peptide library screening have revealed that this specificity resides in the sequence of amino acids flanking the pSer/Thr-Pro sequence. Pin1 binds a Ser/ThrPro-containing motif that is almost identical to that recognized by MPM-2 (Yaffe et al., 1997). This explains the previously puzzling observations that a single monoclonal antibody MPM-2 can specifically recognize a large number of phosphoproteins in species as diverse as humans and plants. Together with the findings that the antibody and Pin1 recognize the overlapping set of phosphoproteins and have similar phenotypes (Shen et al. (1998) *Genes Dev.* 12:706-720), these results indicate that the conservation of the MPM-2 epitope can best be explained by the recognition of this epitope by a highly conserved mitotic regulator, Pin1.

To determine the identity of the Pin1 binding proteins and to gain a sense of the generality of the interaction between Pin1 and phosphoproteins, we used following three different approaches. The first one to probe Pin1-binding proteins with antibodies specific to known phosphoproteins (Shen et al. (1998) *Genes Dev.* 12:706-720). The second one is to obtain peptide sequences of Pin1-binding proteins using microsequencing technique (Lu et al. (1998) *Science* 283:1325-1328). The third one is to phosphorylate a number of in vitro translated mitotic regulators and a recently identified set of mitotic phosphoproteins using *Xenopus* cell cycle extracts, and then determine if they would bind Pin1 (Shen et al. (1998) *Genes Dev.* 12:706-720; Lu et al. (1998) *Science* 283:1325-1328). Pin1 binds a defined subset (about 30) of conserved phosphoproteins, including many important mitotic regulators Cdc25, Wee1, MytI, PlkI, NIMA, tau and Cdc27 (Lu (1999) *Prog. Cell Cycle Res.* (in press).

The WW Domain Mediates the Pin1 Interactions with its Targets by Acting as a Phosphoserine-Binding Module The primary sequence and crystal structural analyses indicate that Pin1 contains two separate domains, PPIase and WW domains (Lu et al. (1996) *Nature* 380:544-7; Ranganathan et al. (1997) *Cell* 89:875-886). The question was raised which-domain confers the unique Pin1 binding specificity. Interestingly, the WW domain contains a hydrophobic cluster, which can be traced to the active site of the PPIase domain by a conserved path of hydrophobicity on the molecular surface (Ranganathan et al. (1997) *Cell* 89:875-886). Given that solvent-exposed hydrophobic patches are generally energetically disfavored in proteins, and are often maintained due to functional necessity, clusters of hydrophobic residues are predicted structural features of protein-protein interaction surfaces (Young et al. (1994) *Protein Sci* 3:717-29; Clackson and Wells (1995) *Science* 267:383-6). Therefore, it is possible that the WW domain plays an important role in targeting Pin1 to the substrates by interacting with phosphoproteins via its hydrophobic patch.

The role of the WW domain in the Pin1 substrate recognition was evaluated by examining the ability of the WW domain to interact with Pin1 target proteins (Lu et al. (1998) *Science* 283:1325-1328). GST-fusion proteins containing Pin1, its WW or PPIase domain were incubated with interphase or mitotic HeLa cell extracts and binding proteins were detected by the MPM-2 monoclonal antibody that recognizes a defined subset of mitotic proteins in a phosphorylation-dependent manner, or by antibodies against specific proteins (Lu et al. (1998) *Science* 283:1325-1328). Interestingly, the Pin1 WW domain, but not the PPIase domain bound almost all of the Pin1-binding proteins.

These results have shown that it is the WW domain that is responsible for binding phosphoproteins and also suggested that the WW domain might be a phosphoserine-binding module. If so, the following four results are expected. First, the interactions between the WW domain and phosphoproteins should depend on phosphorylation of target proteins. Second, the WW domain should bind specific pSer or pThr-containing sequences in the targets. Third, the interactions should be competed by a phosphoserine-containing peptide, but not by the nonphosphorylated counterpart. Finally, the WW domain should display a reasonable affinity for a phosphopeptide. To examine the first prediction, the interactions between Pin1 WW domain and specific target proteins were determined (Lu et al. (1998) *Science* 283:1325-1328). Proteins synthesized in vitro were phosphorylated in a cell cycle specific manner by incubating them with either *Xenopus* interphase or mitotic extracts. Like Pin1, the isolated WW domain bound the Cdc25C that was phosphorylated by mitotic extracts, but not by interphase extracts. However, the WW domain failed to interact with Cdc25C if the mitotically phosphorylated Cdc25C was dephosphorylated prior to the binding (Lu et al. (1998) *Science* 283:1325-1328). These results have demonstrated that the WW domain binding depends on phosphorylation of target proteins.

To determine whether the WW domain of Pin1 binds specific pSer or pThr-containing sequences in target proteins, we screened peptide scan though the whole Pin1-binding protein molecule for the Pin1 WW domain-binding sites, with all conserved Ser/Thr-Pro motifs being synthesized in phosphorylated and nonphosphorylated forms (Lu et al. (1998) *Science* 283:1325-1328). We have found that Pin1 binds very specific phosphorylated Ser/Thr-Pro containing sequences in total 10 of Pin1 target proteins examined so far. For example, the Pin1 WW domain strongly bound to two major phosphorylation sites, Thr48 and Thr67, and did not bind their nonphosphorylated counterparts or other four conserved pSer/Thr sites (Lu et al. (1998) *Science* 283:1325-1328). To confirm these peptide scan results, phosphorylated and nonphosphorylated peptides derived from the Thr-48 region of Cdc25C are synthesized and used to bind the WW domain and to compete with Cdc25C for binding the WW domain. The phosphorylated, but not the nonphosphorylated Thr-48 peptide, directly binds the WW domain with high affinity and is able to compete completely with Cdc25 for WW domain binding (Lu et al. (1998) *Science* 283:1325-1328). Furthermore, double mutant Cdc25C containing Ala substitutions at Thr-48 and Thr-67 completely failed to bind Pin1, although the mutant protein was still phosphorylated by mitotic extracts (Lu et al., unpublished data). Therefore, the Pin1 WW domain binds specific phosphoserine residues present in target proteins.

To examine the ability of a phosphopeptide to compete with phosphoproteins for binding the WW domain, "Pintide" (WFYpSPRLKK), which was originally identified to be the optimal Pin1-binding peptide by screening degenerate peptide libraries (Yaffe et al., 1997), was used. When Pin1 or its WW domain was incubated with various concentrations of Pintide or the control peptide before incubation with mitotic extracts, the phosphoprotein-binding activity was significantly reduced by Pintide, but not with the nonphosphorylated peptide, in a concentration-dependent manner (Lu et al. (1998) *Science* 283:1325-1328). Furthermore, Pintide effectively prevented either Pin1 or the WW domain from binding to MPM2 antigens with a similar potency (Lu et al. (1998) *Science* 283:1325-1328). These results have demonstrated that a phosphopeptide can completely compete with phosphoproteins in binding to Pin1 or its WW domain in a phosphorylation-dependent manner. Finally, to determine the affinity of Pin1 and its different domains for the phosphopeptide, peptides were labeled with fluorescein and their interactions with Pin1 were measured using quantitative fluorescence anisotrophy (Lu et al. (1998) *Science* 283:1325-1328). Pin1 displayed two binding sites for Pintide with different affinities, with Kd being 1.2 and 11.0_m, respectively. Interestingly, the isolated WW domain and PPIase domain had only one binding site and their affinities were corresponding to those of the high and low affinity sites, respectively (Lu et al. (1998) *Science* 283:1325-1328). These results have demonstrated that both the WW domain and the PPIase domain can directly bind the phosphopeptide, with the affinity of the former being much higher than that of the latter. Collectively, the above results demonstrate that the WW domain directly binds with a high affinity to the phosphopeptide and a defined set of phosphoproteins and that these interactions are mediated by specific phosphoserine or threonine residues (Lu et al. (1998) *Science* 283:1325-1328). These properties are reminiscent to those of the SH2 domain and phosphotyrosine interactions (Mayer and Baltimore (1993) *Trends Cell Biol* 3:8-13; Pawson and Schlessinger (1993) *Curr Biol* 3:434-442). Thus, the Pin1 WW domain is a phosphoserine-binding module (Lu et al. (1998) *Science* 283:1325-1328).

Given the essential role of the WW domain in conferring Pin 1-binding specificity in vitro, a critical question is whether this domain is important in vivo. To address this question, we took the advantage that the Pin1 yeast homologue, ESS1/PTF1, is essential for cell growth and that human Pin1 can carry out this essential function (Hanes et al. (1989) *Yeast* 5:55-72; Hard et al., 1995; Lu et al. (1996) *Nature* 380:544-7). A temperature-sensitive ptf1 mutant strain, YPM2, grows at the permissive temperature (23° C.), but not at the restrictive temperature (30° C.) (Hani et al. (1995) *Febs Lett* 365:198-202). This phenotype is completely rescued by PTFI or Pin1 (Lu et al. (1998) *Science* 283:1325-1328). To determine whether the WW domain is important for Pin1 to exert its essential function, the WW domain and the PPIase domain of Pin1 were separately expressed in the same vector, but neither domain was able to complement the ptf1 phenotype (Lu et al. (1998) *Science* 283:1325-1328).

These results indicate that the WW domain is indispensable in vivo. Furthermore, all the WW domain mutants that were able to bind phosphoproteins rescued the ptf1 phenotype. However, all Pin1 mutations, which disrupted the interactions between the Pin1 WW domain and phosphoproteins, abolished the ability of Pin1 to support cell growth (Lu et al. (1998) *Science* 283:1325-1328). These results demonstrate that phosphoprotein-binding activity of the WW domain is essential for Pin1 to function in vivo.

Pin1 Regulates the Biological Function of Phosphoproteins.

Given the fact that Pin1 is a phosphorylation-specific prolyl isomerase that bind a subset of proteins, the obvious question is whether Pin1 affects the function of Pin1-binding proteins. The fact that Pin1 was originally isolated as a protein that physically interacts and Functionally suppresses the mitotic function of the mitotic kinase NIMA, a phosphoprotein and MPM-2 antigen suggests that Pin1 regulates biological activity of its target proteins (Lu et al. (1996) *Nature* 380:544-7). To further address this question, we have chosen two Pin1 target proteins that have well-defined, but different biological activity.

The first target protein is Cdc25C, a phosphatase that dephosphorylates and activates Cdc2 at entry into mitosis (Nurse (1994) *Cell* 79:547-550; King et al. (1994) *Cell* 79:563-571; Lu and Hunter (1995) *Progress in Cell Cycle Research* 1:187-205). Cdc25C is activated by mitosis-specific phosphorylation on the MPM-2 epitopes at the G2/M transition. Since it is the mitotically phosphorylated form of Cdc25C that interacts with Pin1 (Shen et al. (1997) *Proc. Natl. Acad. Sci. USA* 94:13618-13623), it is conceivable that the inhibitory effects of Pin1 on entry into mitosis could be at least partially explained through inhibition of Cdc25C activity. To test this possibility, we first examined whether Pin1 interacts with Cdc25C in vivo and if so, whether this interaction is cell cycle regulated. Both in HeLa cells and *Xenopus* extracts, the interaction between Pin1 and Cdc25C was indeed cell cycle-regulated (Shen et al. (1997) *Proc. Natl. Acad. Sci. USA* 94:13618-13623).

The interaction significantly increased just prior to mitosis. Further experiments using peptide scan has identified that both Pin1 and its WW domain bound only two conserved pSer-Pro sites (Thr-48 and -67), but not other four conserved pSer-Pro sites or their nonphosphorylated counterparts. Significantly, Izumi and Maller (Izumi and Maller (1993) *Mol Biol Cell* 4:1337-50) have identified that phosphorylation of these Thr residues is important for activating Cdc2 and for initiating mitotic entry in *Xenopus* extracts. Significantly, double mutations at these two Thr residues completely abolished the ability of Cdc25C to promote entry into mitosis (Izumi and Maller (1993) *Mol Biol Cell* 4:1337-50), as well as to bind Pin1 (Shen et al. (1997) *Proc. Natl. Acad. Sci. USA* 94:13618-13623; Zhou and Lu unpublished data). These results have shown that Pin1 interacts with the phosphorylation sites on Cdc25C that are essential for its mitotic activation. Finally to examine whether Pin1 can regulate activity of Cdc25C, Pin1 was incubated with the mitotically phosphorylated and active Cdc25c. Pin1 reduced the Cdc25C activity to a level similar to that of Cdc25C incubated with interphase extracts, indicating that Pin1 prevents the mitotic activation of Cdc25C. This offers one explanation for the ability of Pin1 to inhibit mitotic entry.

The second target is tau, a microtubule-binding protein that is important for stabilizing the microtubular structure of cells during mitosis. Although tau is phosphorylated on multiple Ser/Thr sites in vivo, we have demonstrated that Pin1 binds to only one single phosphorylated Thr-Pro motif in tau, pThr231 (Lu et al. (1999) *Nature* (in press)). Upon phosphorylation of tau by many protein kinases, including Cdc2, tau loses its ability to bind microtubules (MTs) and promote MT assembly (Bramblett et al. (1993) *Neuron* 10:1089-99; Yoshida and Ihara (1993) *J Neurochern* 61:1183-6). To examine whether Pin1 can restore the ability of phosphorylated tau to bind MTs, we generated phosphorylated tau in vitro using purified Cdc2, and determined its ability to bind Taxol-stabilized MTs in the presence or absence of Pin1 (Lu et al. (1999) *Nature* (in press)).

Although phosphorylation of tau by Cdc2 disrupted the ability of tau to bind MTs, the binding was fully restored by pre-incubation with Pin1. Furthermore, Pin1 was also detected in the fraction of tau-bound NITs (Lu et al. (1999) *Nature* (in press)). These results demonstrate that Pin1 binds phosphorylated tau and restores its ability to bind MTs. We next assessed the effect of Pin1 on the ability of phosphorylated tau to promote NIT assembly using light-scattering assays (Lu et al. (1999) *Nature* (in press)). The rate of the turbidity change was minimal in the absence of tau, but was dramatically increased if recombinant tau was added. However, the rate of the increase was basically abolished if tau was first phosphorylated by Cdc2. These results confirm that phosphorylation of tau by Cdc2 disrupts its ability to promote NT assembly. Importantly, although Pin1 had no effect on the ability of nonphosphorylated tau to promote MT assembly, Pin1 fully restored the ability of Cdc2 phosphorylated tau to promote MT assembly. In contrast, cyclophilin, a different isomerase had any detectable effects on phosphorylated tau (Lu et al. (1999) *Nature* (in press)). These results have demonstrated that Pin1 not only binds phosphorylated tau, but also functionally restores its biological activity.

Phosphorylation-Dependent Prolyl Isomerization is a Novel Signaling Regulatory Mechanism Protein phosphorylation on Ser/Thr-Pro motifs is a common mechanism critical for regulating various cellular processes, such as progression through different phases of the cell cycle. Proline residues exist in cis or trans conformation and can put kinks into polypeptide chains. We have shown that phosphorylation on Ser/Thr-Pro motifs not only reduces the cis/trans isomerization rate of Ser/Thr-Pro bonds, but also renders peptides resistant to the isomerase action of the conventional prolyl isomerases, cyclophilins and FKBPs. At the same time, proteins containing phosphorylated Ser/Thr-Pro motifs are substrates for the prololyisomerase Pin1. The WW domain of Pin1 acts as a phosphoserine/threonine-binding module binding a defined subset of phosphoproteins, including key mitotic regulators. These interactions target the enzymatic activity of Pin1 close to its substrates. In contrast to other prolyl isomerases, Pin1 has an extremely high degree of substrate specificity, specifically isomerizing phosphorylated Ser/Thr-Pro bonds. Therefore, Pin1 binds and regulates the function of phosphoproteins, some of which are involved in mitosis.

Inhibiting Pin1 function leads to mitotic arrest and apoptosis in yeast and human cells. The results suggest a new two-step mechanism for mitotic regulation. The first event is phosphorylation at specific Ser-Pro or Thr-Pro sites by the mitosis-specific activation of Pro-directed protein kinases. However, the resulting pSer/Thr-Pro moieties are likely to prefer different conformations from the Ser or Thr residues. This is because relaxation to a new stable conformation is limited by the reduced prolyl isomerization of the pSer/Thr-Pro bond resulted from addition of the phosphate group.

Thus, these phosphoproteins are likely to exist in a different conformation until Pin1 binds and relaxes the structures. Pin1 would determine the duration of the certain conformational state of mitotic phosphoproteins. These local conformational changes night regulate the activity of a phosphoprotein, such as Cdc25, and NIMA, alter the ability of a phosphoprotein to interact with other proteins, such as tau, to be dephosphorylated or to be degraded, or change the subcellular localization of a phosphoprotein. Therefore, in contrast to the other prolyl isomerases, whose primary function is to facilitate post-translational folding events, the Pin1 subfamily of prolyl isomerase is used to regulate the function of proteins after proteins have been fully folded and phosphorylated.

Uses and Methods of the Invention

The Pin1 markers (e.g., Pin1 nucleic acid molecules, Pin1 proteins, Pin1 protein homologues, and/or Pin1 antibodies) described herein can be used in one or more methods which relate to Pin1-associated disorders, including: a) screening assays; b) predictive medicine (e.g., diagnostic assays, prognostic assays, monitoring clinical trials, and pharmacogenetics); and c) methods of treatment (e.g., therapeutic and prophylactic).

As used herein, the term "Pin1-associated disorder" includes a disorder or a state (e.g., a disease state) which is associated with abnormal cell growth, abnormal cell proliferation, or aberrant levels of Pin1 marker. Pin1-associated disorders include cancers, malignancies, tumors, and proliferative arthritic conditions. Pin1-associated disorders further include disorders which are not specific to a given tissue or cell type (e.g., a Pin1-associated disorder may present in a variety of tissues or cell types).

As used herein, the term "abnormal cell growth" is intended to include cell growth which is undesirable or inappropriate. Abnormal cell growth also includes proliferation which is undesirable or inappropriate (e.g., unregulated cell proliferation or undesirably rapid cell proliferation). Abnormal cell growth can be benign and result in benign masses of tissue or cells, or benign tumors. Many art-recognized conditions are associated with such benign masses or benign tumors including diabetic retinopathy, retrolental fibroplasia, neovascular glaucoma, psoriasis, angiofibromas, rheumatoid arthritis, hemangiomas, and Karposi's sarcoma. Abnormal cell growth can also be malignant and result in malignancies, malignant masses of tissue or cells, or malignant tumors. Many art-recognized conditions and disorders are associated with malignancies, malignant masses, and malignant tumors including cancer and carcinoma.

As used herein, the term "tumor" is intended to encompass both in vitro and in vivo tumors that form in any organ of the body. Tumors may be associated with benign abnormal cell growth (e.g., benign tumors) or malignant cell growth (e.g., malignant tumors). The tumors which are described herein are preferably sensitive to the Pin1 inhibitors of the present invention. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys.

As used herein, the term "Pin1 marker" refers to a marker which is capable of being indicative of Pin1 levels in a sample of the invention. Pin1 markers include nucleic acid molecules (e.g., mRNA, DNA) which corresponds to some or all of a Pin1 gene, peptide sequences (e.g., amino acid sequences) which correspond to some or all of a Pin1 protein, peptide sequences which are homologous to Pin1 peptide sequences, antibodies to Pin1 protein, substrates of Pin1 protein, binding partners of Pin1 protein, and activity of Pin1.

The isolated nucleic acid molecules of Pin1 can be used, for example, to express Pin1 protein, to detect Pin1 mRNA (e.g., Pin1 nucleic acid marker in a biological sample) or a genetic alteration in a Pin1 gene, or to modulate Pin1 activity, as described further below. The Pin1 proteins can be used to treat disorders characterized by insufficient or excessive production of Pin1 or a Pin1 substrate by the use of inhibitors and/or modulators (e.g., abnormal or malignant cell growth, tumors, cancer). In addition, the Pin1 proteins can be used to screen for naturally occurring Pin1 substrates, to screen for drags or compounds which modulate Pin1 activity, as well as to treat disorders characterized by insufficient or excessive production of Pin1 protein or production of Pin1 protein forms which have decreased or aberrant activity compared to Pin1 wild type protein. Moreover, the anti-Pin1 antibodies of the invention can be used to detect and isolate Pin1 proteins, regulate the bioavailability of Pin1 proteins, and modulate Pin1 activity.

A. Screening Assays for Modulators and/or Inhibitors:

One major goal in cancer treatment has been to prevent the unregulated cell proliferation and, even better, to specifically kill dividing cancer cells. Interestingly, mitotic checkpoint controls have been identified as key targets for anticancer therapeutic procedures for two major reasons. First, since mitosis is a tightly regulated and orderly process, anticancer drugs that target at mitotic checkpoint controls can kill cells, often by inducing mitotic arrest followed by apoptosis. This is in contrast to those anticancer drugs that target other phase of the cell cycle, which just stop cells from continuous growing, but do not kill them. One of the best examples is the microtubule modifying agents, such as Oncovin and Taxols, which have been proven to be powerful drugs in treating various tumors (Piccart and Di Leo (1997) *Semin Oncol* 24:S10-27-S10-33). Second, abrogation of G2/M checkpoint have been shown to improve radiation therapy (Meyn (1997) *Oncology* 11:349-56 (see also discussion on pages 356, 361 and 365); Muschel et al. (1997) *Vitam Horm* 53:1-25). Since effective radiation therapy has been shown to induces cell cycle arrest in G2 and M, and subsequent apoptosis, drugs that disrupt mitotic checkpoints would have a cooperative effect with irradiation in killing cancer cells. For at least the following reasons, Pin1 is be a potential novel drug target.

1) One of the most important reasons relies on the unique features of Pin1 that are distinct from the other well known PPIases cyclophins and FKBPs. Although Cyclophilins and FKBPs have been shown to be involved in some protein folding process, they have low substrate specificity and also are not essential genes for cell survival. Furthermore, in spite of the fact that they are well known cellular receptors for the clinically relevant immunosuppressive drugs cyclosporin A and FK506, inhibition of the PPIase activity of neither cyclophilins nor FKBPs of the PPIase activity is unrelated to the immunosuppressive property of the drug/PPIase complexes. Therefore, evidence for the biological importance of PPIase activity of cyclophilins and FKBPs remains to be elucidated. In contrast, the Pin1 subfamily of PPIases is the first documented PPIase that is essential for cell survival, and which participates in the control of the timing of mitosis. Furthermore, this new subfamily of PPIases has extremely high substrate specificity.

This novel substrate specificity is conferred by its unique protein-targeting WW domain and its distinct structure in the active site. Pin1 catalyze a prolyl isomerization of the phosphorylated Ser/Thr-Pro bond, a reaction that is substantially slowed down due to phosphorylation by Pro-directed kinases, but at the same time, is resistant to the action of cyclophilins or FKBPs. Therefore, Pin1 is a novel post-phosphorylation regulator that controls the function of a protein that has been phosphorylated, but has not been dephosphorylated.

2) Since Pin1 targets include a defined subset of mitosis-specific phosphoproteins, Pin1 targets are present in dividing mitotic cells, but not in other phases of the cell cycle. This suggests that Pin1 inhibitors do not likely affect the vast majority of normal cells, but rather specifically attach only a small window of the cell division cycle.

3) A novel phosphoserine-binding module in Pin1 has been discovered which is essential for mediating the specific interactions between Pin1 and the mitotic substrate. High affinity (Kd=10 nM) peptide ligands (Pintides) have been identified, confirming the specificity of this module and opening a new avenue for designing specific inhibitors.

4) Detailed substrate specificity analyses, together with the high-resolution crystal structure of Pin1 complexed with a substrate peptide, have demonstrated that Pin1 has easily measured prolyl isomerase activity that is specific the phosphorylated Ser/Thr-Pro peptide bond.

5) Importantly, inhibition of Pin1 by depletion or antisense polyoligonucleotides kills cells by inducing mitotic arrest and apoptosis (Lu et al. (1996) *Nature* 380:544-7). These results indicate that Pin1 inhibitors might be lethal specifically to the dividing cancer cells in mitosis.

6) Pin1 participates in the control of the timing of mitotic entry. Pin1 binds and regulates the function of at least three of mitosis-specific phosphoproteins, Cdc25C, NIMA and tau. It has been demonstrated that Pin1 inhibits mitotic activation of Cdc25C and plays an essential role on regulating the timing of Cdc2 activation and mitotic entry. This is consistent with the findings that inhibition of Pin1 induces premature mitotic entry.

7) Pin1 is overexpressed in human breast cancer samples and its levels are correlated with the nuclear grade of tumors, as described above. These results suggest that Pin1 inhibitors are likely to have more selectivity to kill cancer cells.

8) The prolylisomerase activity of Pin1 is essential for cell function. In the light of the surprising findings that disruption of all known 12 conventional prolyl isomerase genes, 8 cyclophins and 4 FKBPs has, in one cell has little effect on cell growth, the cellular function of prolyl isomerase activity remains elusive. In contrast, disruption of the single Pin1 homologue Ess1/Ptf1 is lethal. Since Pin1 contains the phosphoprotein-binding WW domain that is essential for cell survival, the KEY question is whether prolyl isomerase activity is required for cell survival. To address this question, we introduced a large number of mutations into Pin1 both by random and site-directed mutagenesis and examined their effects on the ability of Pin1 to rescue the temperature-sensitive Ess1/Ptf1 mutation in yeast. Our results have convincingly demonstrated that the prolyl isomerase activity of Pin1 is required for Pin1 to carry out its essential function and is essential for phosphorylation signaling. These results suggest that reagents that inhibit the prolyl isomerase activity are likely to kill mitotically dividing cells.

As such, the invention provides a method (also referred to herein as a "screening assay") for identifying modulators, i.e., candidate or test compounds or agents (e.g., peptides, peptidomimetics, small molecules or other drugs) which bind to Pin1 proteins, have a stimulatory or inhibitory effect on, for example, Pin1 expression or Pin1 activity, or have a stimulatory or inhibitory effect on, for example, the expression or activity of a Pin1 substrate.

In one embodiment, the invention provides assays for screening candidate or test compounds which are substrates of a Pin1 protein or polypeptide or biologically active portion thereof or which can bind to a Pin1 protein or polypeptide or biologically active portion thereof. In another embodiment, the invention provides assays for screening candidate or test compounds to identify Pin1 modulators. As used herein, a Pin1 modulator includes a molecule or peptide or compound which can modulate the activity of a Pin1 protein or polypeptide or biologically active portion thereof. Pin1 modulators include inhibitors of Pin1 and activators of Pin1. Test compounds for such screening can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In another embodiment, an assay is a cell-based assay comprising contacting a cell expressing a Pin1 target molecule (e.g., a Pin1 substrate; a phosphoprotein) with a test compound and determining the ability of the test compound to modulate (e.g. stimulate or inhibit) the activity of the Pin1 target molecule. Determining the ability of the test compound to modulate the activity of a Pin1 target molecule can be accomplished, for example, by determining the ability of the Pin1 protein to bind to or interact with the Pin1 target molecule, or by determining the ability of the Pin1 protein to isomerize the Pin1 target molecule.

Determining the ability of the Pin1 protein to bind to or interact with a Pin1 target molecule can be accomplished by determining direct binding. Determining the ability of the Pin1 protein to bind to or interact with a Pin1 target molecule can be accomplished, for example, by coupling the Pin1 protein with a radioisotope or enzymatic label such that binding of the Pin1 protein to a Pin1 target molecule can be determined by detecting the labeled Pin1 protein in a complex. For example, Pin1 molecules, e.g., Pin1 proteins, can be labeled with $^{125}$I, $^{35}$S, $^{14}$C, or $^{3}$H, either directly or indirectly, and the radioisotope detected by direct counting of radioemmission or by scintillation counting. Alternatively, Pin1 molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between Pin1 and its target molecule, without the labeling of any of the interactants. For example, a microphysiometer can be used to detect the interaction of Pin1 with its target molecule without the labeling of either Pin1 or the target molecule. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the Pin1 protein to bind to or interact with a Pin1 target molecule can be accomplished by determining the activity of the target molecule. For example, the activity of the target molecule can be determined by detecting induction of a downstream event (e.g., expression of cyclin D1, mitosis etc.), detecting catalytic/enzymatic activity of the target an appropriate substrate, detecting the induction of a reporter gene (comprising a target-responsive regulatory element (e.g. AP-1) operatively linked to a nucleic acid encoding a detectable marker, e.g., chloramphenicol acetyl transferase), or detecting a target-regulated cellular response.

In yet another embodiment, an assay of the present invention is a cell-free assay in which a Pin1 protein or biologically active portion thereof is contacted with a test compound and the ability of the test compound to bind to the Pin1 protein or biologically active portion thereof is determined. Binding of the test compound to the Pin1 protein can be determined either directly or indirectly as described above. In a preferred embodiment, the assay includes contacting the Pin1 protein or biologically active portion thereof with a known compound which binds Pin1 to form an assay mixture, contacting the assay mixture with a test compound, and determining the ability of the test compound to interact with a Pin1 protein, wherein determining the ability of the test compound to interact with a Pin1 protein comprises determining the ability of the test compound to preferentially bind to Pin1 or biologically active portion thereof as compared to the known compound.

In another embodiment, the assay is a cell-free assay in which a Pin1 protein or biologically active portion thereof is contacted with a test compound and the ability of the test compound to modulate (e.g., stimulate or inhibit) the activity of the Pin1 protein or biologically active portion thereof is determined. Determining the ability of the test compound to modulate the activity of a Pin1 protein can be accomplished, for example, by determining the ability of the Pin1 protein to bind to a Pin1 target molecule by one of the methods described above for determining direct binding. Determining the ability of the Pin1 protein to bind to a Pin1 target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a Pin1 protein can be accomplished by determining the ability of the Pin1 protein to further modulate the isomerization of the activity of a Pin1 target molecule (e.g., a Pin1 substrate, a phosphoprotein). For example, the activity of the effector molecule on an appropriate target can be determined, or the binding of the effector to an appropriate target can be determined as previously described.

In yet another embodiment, the cell-free assay involves contacting a Pin1 protein or biologically active portion thereof with a known compound which binds the Pin1 protein to form an assay mixture, contacting the assay mixture with a test compound, and determining the ability of the test compound to interact with the Pin1 protein, wherein determining the ability of the test compound to interact with the Pin1 protein comprises determining the ability of the Pin1 protein to preferentially bind to or modulate the activity of a Pin1 target molecule.

The cell-free assays of the present invention are amenable to use of both soluble and/or membrane-bound forms of proteins (e.g., Pin1 proteins or biologically active portions thereof, or receptors to which Pin1 binds). In the case of cell-free assays in which a membrane-bound form a protein is used (e.g., a cell surface Pin1 receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either Pin1 or its target molecule to facilitate separation of complexed from uncomplexed forms of one or both of the proteins, as well as to accommodate automation of the assay. Binding of a test compound to a Pin1 protein, or interaction of a Pin1 protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/Pin1 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or Pin1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of Pin1 binding or activity determined using standard techniques.

Other techniques for immobilizing proteins on matrices can also be used in the screening assays of the invention. For example, either a Pin1 protein or a Pin1 target molecule can be immobilized utilizing conjugation of biotin and streptavidin. Biotinylated Pin1 protein or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical).

Alternatively, antibodies reactive with Pin1 protein or target molecules but which do not interfere with binding of the Pin1 protein to its target molecule can be derivatized to the wells of the plate, and unbound target or Pin1 protein trapped in the wells by antibody conjugation. Methods for detecting such complexes, in addition to those described above for the GST-immobilized complexes, include immunodetection of complexes using antibodies reactive with the Pin1 protein or target molecule, as well as enzyme-linked assays which rely on detecting an enzymatic activity associated with the Pin1 protein or target molecule.

In another embodiment, Pin1 modulators are identified in a method wherein a cell is contacted with a candidate compound and the expression of Pin1 mRNA or protein in the cell is determined. The level of expression of Pin1 mRNA or protein in the presence of the candidate compound is compared to the level of expression of Pin1 mRNA or protein in the absence of the candidate compound. The candidate compound can then be identified as a modulator of Pin1 expression based on this comparison. For example, when expression of Pin1 mRNA or protein is greater (statistically significantly greater) in the presence of the candidate compound than in its absence, the candidate compound is identified as a stimulator of Pin1 mRNA or protein expression. Alternatively, when expression of Pin1 mRNA or protein is less (statistically significantly less) in the presence of the candidate compound than in its absence, the candidate compound is identified as an inhibitor of Pin1 mRNA or protein expression The level of Pin1 mRNA or protein expression in the cells can be determined by methods described herein for detecting Pin1 mRNA or protein.

In yet another aspect of the invention, the Pin1 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with Pin1 ("Pin1-binding proteins" or "Pin1-bp") and are involved in Pin1 activity. Such Pin1-binding proteins are also likely to be involved in the propagation of signals by the Pin1 proteins or Pin1 targets as, for example, downstream elements of a Pin1-mediated signaling pathway. Alternatively, such Pin1-binding proteins are likely to be Pin1 inhibitors.

The two-hybrid system is based on the modular nature of most transcription factors, which consist of separable DNA-binding and activation domains. Briefly, the assay utilizes two different DNA constructs. In one construct, the gene that codes for a Pin1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Pin1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Pin1 protein.

This invention further pertains to novel agents identified by the above-described screening assays. Accordingly, it is within the scope of this invention to further use an agent identified as described herein in an appropriate animal model. For example, an agent identified as described herein (e.g., a Pin1 modulating agent, an antisense Pin1 nucleic acid molecule, a Pin1-specific antibody, or a Pin1-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for measuring levels of Pin1 marker, as well as Pin1 activity, in the context of a biological sample to thereby determine whether an individual is afflicted with a disease or disorder, or is at risk of developing a disorder, associated with aberrant Pin1 expression or activity (e.g. abnormal or indignant cell growth, tumors, cancer). The invention also provides for prognostic (or predictive) assays for determining whether an individual is at risk of developing a disorder associated with a Pin1 marker. The invention further provides for prognostic (or predictive) assays for determining the stage of a Pin1-associated disorder.

As used herein, the term "stage" includes the degree of progression of a disease. Examples of Pin1-associated disorders which may have stages assigned to them include cancers, malignancies, abnormal cell growth, and tumors. Considerations for assigning stages to such disorders include level of metastases (if metastatic at all) of a cancer or malignancy, and level of aggressiveness of a cancer or malignancy. Other generally accepted criteria for assigning stages to such disorders are well known to one skilled in the art.

Another aspect of the invention pertains to monitoring the effectiveness of agents (e.g., drugs, compounds, anti-cancer agents) on the expression or activity of Pin1 in clinical trials.

These and other agents are described in further detail in the following sections.

1. Diagnostic Assays

An exemplary method for detecting the presence or absence of Pin1 protein or nucleic acid in a biological sample involves obtaining a biological sample from a test subject and contacting the biological sample with a compound or an agent capable of detecting Pin1 protein or nucleic acid (e.g., mRNA, genomic DNA) that encodes Pin1 protein such that the presence of Pin1 protein or nucleic acid is detected in the biological sample. A preferred agent for detecting Pin1 mRNA or genomic DNA is a labeled nucleic acid probe capable of hybridizing to Pin1 mRNA or DNA. The nucleic acid probe can be, for example, a Pin1 nucleic acid or a corresponding nucleic acid such as an oligonucleotide of at least 15, 30, 50, 100, 250 or 500 nucleotides in length which is capable of specifically hybridizing under stringent conditions to Pin1 mRNA or genomic DNA. Other suitable probes for use in the diagnostic assays of the invention are described herein.

A preferred agent for detecting Pin1 marker is an antibody capable of binding to Pin1 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

With respect to antibody-based detection techniques, one of skill in the art can raise anti-Pin1 antibodies against an appropriate immunogen, such as isolated and/or recombinant Pin1 or a portion or fragment thereof (including synthetic molecules, such as synthetic peptides) using no more than routine experimentation. Synthetic peptides can be designed and used to immunize animals, such as rabbits and mice, for antibody production. The nucleic and amino acid sequence of Pin1 is known (Hunter et al., WO 97/17986 (1997); Hunter et al., U.S. Pat. Nos. 5,952,467 and 5,972,697, the teachings of all of which are hereby incorporated by reference in their entirety) and can be used to design nucleic acid constructs for producing proteins for immunization or in nucleic acid detection methods or for the synthesis of peptides for immunization.

Conditions for incubating an antibody with a test sample can vary depending upon the tissue or cellular type. Incubation conditions can depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques," Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of enzyme Immunoassays: Laboratory Techniques in Biochemistry and Molecular Biology," is Elsevier Science Publishers, Amsterdam, The Netherlands (1985).

As used herein, the terms "sample" and "biological sample" include samples obtained from a mammal or a subject containing Pin1 which can be used within the methods described herein, e.g., tissues, cells and biological fluids isolated from a subject, as well as tissues, cells and fluids present within a subject. Typical samples from a subject include tissue samples, tumor samples, blood, urine, biopsies, lymph, saliva, phlegm, pus, and the like. Accordingly, the detection method of the invention can be used to detect Pin1 mRNA, protein, or genomic DNA in a biological sample in vitro as well as in vivo. For example, in vitro techniques for detection of Pin1 mRNA include Northern hybridizations and in situ hybridizations. In vitro techniques for detection of Pin1 protein include enzyme linked immunosorbent assays (ELISAs), Western blots, immunoprecipitations and immunofluorescence. In vitro techniques for detection of Pin1 genomic DNA include Southern hybridizations. Furthermore, in vivo techniques for detection of Pin1 protein include introducing into a subject a labeled anti-Pin1 antibody. For example, the antibody can be labeled with a radioactive marker whose presence and location in a subject can be detected by standard imaging techniques.

In another embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Pin1 marker such that the presence of Pin1 marker is detected in the biological sample, and comparing the presence of Pin1 marker in the control sample with the presence of Pin1 marker in the test sample.

The immunological assay test samples of the present invention may include cells, protein or membrane extracts of cells, blood or biological fluids such as ascites fluid or brain fluid (e.g., cerebrospinal fluid). The test sample used in the above-described method is based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized. The invention also encompasses kits for detecting the presence of Pin1 in a biological sample. For example, the kit can comprise a labeled compound or agent capable of detecting Pin1 protein or mRNA in a biological sample; means for determining the amount of Pin1 in the sample; and means for comparing the amount of Pin1 in the sample with a standard. The compound or agent can be packaged in a suitable container. The kit can further comprise instructions for using the kit to detect Pin1 protein or nucleic acid.

A compartmentalized kit can include any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe, primers or antibodies used in the assay, containers which contain wash reagents (such as phosphate buffered saline, Tris-buffers, and the like), and containers which contain the reagents used to detect the hybridized probe, bound antibody, amplified product, or the like.

The kits are used to detect and distinguish normal cells from cells undergoing abnormal cell growth. Additionally, or alternatively, the kits are used to distinguish between aggressive or various stages of an abnormal cell growth (e.g., breast, prostate, liver, lung, kidney, digestive track, ovarian, testicular, skin cancer) or to distinguish between benign or malignant forms of abnormal cell growth in tumors. It is also envisioned that the kits and methods of the invention can be used to define the need for treatment of abnormal cell growths, such as surgical interventions, types of chemotherapeutic drugs or radiation treatments.

The kits and methods of the invention are used to detect metastasis of abnormally cell growths. A "metastasis" is the spread of an abnormal cell growth from one part of the body (e.g., breast tissue, prostate gland, uterus, skin, testes, ovary) to another part of the body (e.g., breast, prostate, uterus, brain, skin, testes, ovary, lymph nodes).

One skilled in the art will readily recognize that the nucleic acid probes described in the present invention can readily be incorporated into one of the established kit formats which are well known in the art.

In the embodiments of the invention described herein, well known biomolecular methods such as northern blot analysis, RNase protection assays, southern blot analysis, western blot analysis, in situ hybridization, immunocytochemical procedures of tissue sections or cellular spreads, and nucleic acid amplification reactions (e.g., polymerase chain reactions) may be used interchangeably. One of skill in the art would be capable of performing these well-established protocols for the methods of the invention. (See, for example, Ausubel, et al., "Current Protocols in Moleculer Biology," John Wiley & Sons, NY, N.Y. (1999)).

2. Prognostic Assays

The diagnostic methods described herein can furthermore be utilized to identify subjects having or at risk of developing a disease or disorder associated with aberrant Pin1 expression or activity. For example, the assays described herein, such as the preceding diagnostic assays or the following assays, can be utilized to identify a subject having or at risk of developing a disorder associated with Pin1 marker (e.g., abnormal or malignant cell growth, tumors, cancer). Thus, the present invention provides a method for identifying a disease or disorder associated with aberrant Pin1 expression or activity in which a test sample is obtained from a subject and Pin1 protein or nucleic acid (e.g., mRNA, genomic DNA) is detected, wherein the presence of Pin1 protein or nucleic acid is diagnostic for a subject having or at risk of developing a Pin1-associated disorder.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Pin1 expression or activity. Thus, the present invention provides methods for determining whether a subject can be effectively treated with an agent for a disorder associated with aberrant Pin1 expression or activity in which a test sample is obtained and Pin1 protein or nucleic acid expression or activity is detected (e.g., wherein the abundance of Pin1 protein or nucleic acid expression or activity is diagnostic for a subject that can be administered the agent to treat a disorder Pin1-associated disorder).

The methods of the invention can also be used to detect genetic alterations in a Pin1 gene, thereby determining if a subject with the altered gene is at risk for a disorder associated with the Pin1 gene. In preferred embodiments, the methods include detecting, in a sample of cells from the subject, the presence or absence of a genetic alteration characterized by at least one of an alteration affecting the integrity of a gene encoding a Pin1-protein, or the mis-expression of the Pin1 gene. For example, such genetic alterations can be detected by ascertaining the existence of at least one of 1) a deletion of one or more nucleotides from a Pin1 gene; 2) an addition of one or more nucleotides to a Pin1 gene; 3) a substitution of one or more nucleotides of a Pin1 gene, 4) a chromosomal rearrangement of a Pin1 gene; 5) an alteration in the level of a messenger RNA transcript of a Pin1 gene, 6) aberrant modification of a Pin1 gene, such as of the methylation pattern of the genomic DNA, 7) the presence of a non-wild type splicing pattern of a messenger RNA transcript of a Pin1 gene, 8) a non-wild type level of a Pin1-protein, 9) allelic loss of a Pin1 gene, and 10) inappropriate post-translational modification of a Pin1-protein. As described herein, there are a large number of assay techniques known in the art which can be used for detecting alterations in a Pin1 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683, 202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the Pin1-gene (see Abravaya et al. (1995) *Nucleic Acids Res* 0.23:675-682). This method can include the steps of collecting a sample from a patient, isolating nucleic acid (e.g., genomic, mRNA or both) from the sample, contacting the nucleic acid sample with one or more primers which specifically hybridize to a Pin1 gene under conditions such that hybridization and amplification of the Pin1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al, (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Pin1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Pin1 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in Pin1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Pin1 gene and detect mutations by comparing the sequence of the sample Pin1 with the corresponding wild-type (control) sequence. Examples of sequencing reactions include those based on techniques developed by Maxam and Gilbert ((1977) *Proc. Natl. Acad. Sci. USA* 74:560) or Sanger ((1977)

*Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g. PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the Pin1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type Pin1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Pin1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a Pin1 sequence, e.g., a wild-type Pin1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Pin1 genes. For example, single strand conformation polymorphism (SSCP) may be used to detect differences in electrophoretic mobility between mutant and wild type nucleic acids (Orita et al. (1989) *Proc Natl. Acad. Sci. USA:* 86:2766, see also Cotton (1993) *Mutat Res* 285:125-144; and Hayashi (1992) *Genet Anal Tech Appl* 9:73-79). Single-stranded DNA fragments of sample and control Pin1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Pin1 gene.

Furthermore, any cell type or tissue in which Pin1 is expressed may be utilized in the prognostic assays described herein.

3. Monitoring of Effects During Clinical Trials

Monitoring the influence of agents (e.g., drugs or compounds) on the expression or activity of a Pin1 protein can be applied not only in basic drug screening, but also in clinical trials. For example, the effectiveness of an agent determined by a screening assay as described herein to increase Pin1 gene expression, protein levels, or upregulate Pin1 activity, can be monitored in clinical trials of subjects exhibiting decreased Pin1 gene expression, protein levels, or downregulated Pin1 activity. Alternatively, the effectiveness of an agent determined by a screening assay to decrease Pin1 gene expression, protein levels, or downregulate Pin1 activity, can be monitored in clinical trials of subjects exhibiting increased Pin1 gene expression, protein levels, or upregulated Pin1 activity. In such clinical trials, the expression or activity of a Pin1 gene, and preferably, other genes that have been implicated in a disorder can be used as a "read out" or markers of the phenotype of a particular cell.

For example, and not by way of limitation, genes, including Pin1, that are modulated in cells by treatment with an agent (e.g., compound, drug or small molecule) which modulates Pin1 activity (e.g., identified in a screening assay as described herein) can be identified. Thus, to study the effect of agents on a Pin1 associated disorder, for example, in a clinical trial, cells can be isolated and RNA prepared and analyzed for the levels of expression of Pin1 and other genes implicated in the Pin1 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Pin1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression or activity of a Pin1 protein, mRNA, or genomic DNA in the pre-administration sample; (iii) obtaining one or more post-administration samples from the subject; (iv) detecting the level of expression or activity of the Pin1 protein, mRNA, or genomic DNA in the post-administration samples; (v) comparing the level of expression or activity of the Pin1 protein, mRNA, or genomic DNA in the pre-administration sample with the Pin1 protein, mRNA, or genomic DNA in the post administration sample or samples; and (vi) altering the administration of the agent to the subject accordingly. For example, increased administration of the agent may be desirable to increase the expression or activity of Pin1 to higher levels than detected, i.e., to increase the effectiveness of the agent. Alternatively, decreased administration of the agent may be desirable to decrease expression or activity of Pin1 to lower levels than detected, i.e. to decrease the effectiveness of the agent. According to such an embodiment, Pin1 expression or activity may be used as an indicator of the effectiveness of an agent, even in the absence of an observable phenotypic response.

C. Methods of Treatment:

The present invention provides for both prophylactic and therapeutic methods of treating a subject at risk of (or susceptible to) a disorder or having a disorder associated with aberrant Pin1 expression or activity (e.g., abnormal or malignant cell growth, tumors, cancer).

"Treatment", as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the Pin1 molecules of the present invention or Pin1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant Pin1 expression or activity, by administering to the subject a Pin1 or an agent which modulates Pin1 expression or at least one Pin1 activity. Subjects at risk for a disease which is caused or contributed to by aberrant Pin1 expression or activity can be identified by, for example, any or a combination of diagnostic or prognostic assays as described herein. Administration of a prophylactic agent can occur prior to the manifestation of symptoms characteristic of the Pin1 aberrancy, such that a disease or disorder is prevented or, alternatively, delayed in its progression. Depending on the type of Pin1 aberrancy, for example, a Pin1, Pin1 agonist or Pin1 antagonist agent can be used for treating the subject. The appropriate agent can be determined based on screening assays described herein.

2. Therapeutic Methods

Another aspect of the invention pertains to methods of modulating Pin1 expression or activity for therapeutic purposes. Accordingly, in an exemplary embodiment, the modulatory method of the invention involves contacting a cell with a Pin1 or agent that modulates one or more of the activities of Pin1 protein activity associated with the cell. An agent that modulates Pin1 protein activity can be an agent as described herein, such as a nucleic acid or a protein, a naturally-occurring target molecule of a Pin1 protein (e.g., a phosphoprotein), a Pin1 antibody, a Pin1 agonist or antagonist, a peptidomimetic of a Pin1 agonist or antagonist, or other small molecule. In one embodiment, the agent stimulates one or more Pin1 activities. Examples of such stimulatory agents include active Pin1 protein and a nucleic acid molecule encoding Pin1 that has been introduced into the cell. In another embodiment, the agent inhibits one or more Pin1 activities. Examples of such inhibitory agents include antisense Pin1 nucleic acid molecules, anti-Pin1 antibodies, and Pin1 inhibitors. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a Pin1 protein or nucleic acid molecule. In one embodiment, the method involves administering an agent (e.g., an agent identified by a screening assay described herein), or combination of agents that modulates (e.g., upregulates or downregulates) Pin1 expression or activity. In another embodiment, the method involves administering a Pin1 protein or nucleic acid molecule as therapy to compensate for reduced or aberrant Pin1 expression or activity.

Stimulation of Pin1 activity is desirable in situations in which Pin1 is abnormally downregulated and/or in which increased Pin1 activity is likely to have a beneficial effect. For example, stimulation of Pin1 activity is desirable in situations in which a Pin1 is downregulated and/or in which increased Pin1 activity is likely to have a beneficial effect. Likewise, inhibition of Pin1 activity is desirable in situations in which Pin1 is abnormally upregulated and/or in which decreased Pin1 activity is likely to have a beneficial effect.

The present invention further includes therapeutic methods which utilize a combination of therapeutic agents of the invention, as described herein, and further therapeutic agents which are known in the art. Specifically, a Pin1 modulator of the present invention can be used in combination with a second modulator or with a second "abnormal cell growth inhibitory agent" (ACI agent). The ACI agent can be any therapeutic agent which can be used to treat the selected Pin1-associated disorder and/or cancer. One skilled in the art would be able to select appropriate ACI agents for combination therapy with a Pin1 modulator. For example, an ACI agent may be a second Pin1 modulator, or it may be an art-recognized agent which does not modulate Pin1.

The terms "abnormal cell growth inhibitory agent" and "ACI agent" are used interchangeably herein and are intended to include agents that inhibit the growth of proliferating cells or tissue wherein the growth of such cells or tissues is undesirable. For example, the inhibition can be of the growth of malignant cells such as in neoplasms or benign cells such as in tissues where the growth is inappropriate. Examples of the types of agents which can be used include chemotherapeutic agents, radiation therapy treatments and associated radioactive compounds and methods, and immunotoxins.

The language "chemotherapeutic agent" is intended to include chemical reagents which inhibit the growth of proliferating cells or tissues wherein the growth of such cells or tissues is undesirable. Chemotherapeutic agents are well known in the art (see e.g., Gilman A. G., et al., *The Pharmacological Basis of Therapeutics* 8th Ed., Sec 12:1202-1263 (1990)), and are typically used to treat neoplastic diseases, tumors, and cancers.

The language "radiation therapy" is intended to include the application of a genetically and somatically safe level of x-rays, both localized and non-localized, to a subject to inhibit, reduce, or prevent symptoms or conditions associated with undesirable cell growth. The term x-rays is intended to include clinically acceptable radioactive elements and isotopes thereof, as well as the radioactive emissions therefrom. Examples of the types of emissions include alpha rays, beta rays including hard betas, high energy electrons, and gamma rays. Radiation therapy is well known in the art (see e.g., Fishbach, F., *Laboratory Diagnostic Tests* 3rd Ed., Ch. 10: 581-644 (1988)), and is typically used to treat neoplastic diseases, tumors, and cancers.

The term "immunotoxins" includes immunotherapeutic agents which employ cytotoxic T cells and/or antibodies, e.g., monoclonal, polyclonal, phage antibodies, or fragments thereof, which are utilized in the selective destruction of undesirable rapidly proliferating cells. For example, immunotoxins can include antibody-toxin conjugates (e.g., Ab-ricin and Ab-diphtheria toxin), antibody-radiolabels (e.g., Ab-$I^{135}$) and antibody activation of the complement at the tumor cell. The use of immunotoxins to inhibit, reduce, or prevent symptoms or conditions associated with neoplastic diseases are well known in the art (see e.g., Harlow, E. and Lane, D., *Antibodies*, (1988)).

The language "inhibiting undesirable cell growth" is intended to include the inhibition of undesirable or inappropriate cell growth. The inhibition is intended to include inhibition of proliferation including rapid proliferation. For example, the cell growth can result in benign masses or the inhibition of cell growth resulting in malignant tumors. Examples of benign conditions which result from inappropriate cell growth or angiogenesis are diabetic retinopathy, retrolental fibroplasia, neovascular glaucoma, psoriasis, angiofibromas, rheumatoid arthritis, hemangiomas, Karposi's sarcoma, and other conditions or dysfunctions characterized by dysregulated endothelial cell division.

3. Pharmacogenomics

The Pin1 molecules of the present invention, as well as agents, or modulators which have a stimulatory or inhibitory effect on Pin1 activity (e.g., Pin1 gene expression) as identified by a screening assay described herein can be administered to individuals to treat (prophylactically or therapeutically) disorders (e.g, proliferative disorders such as cancer) associated with aberrant Pin1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a Pin1 molecule or Pin1 modulator as well as tailoring the dosage and/or therapeutic regimen of treatment with a Pin1 molecule or Pin1 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g. a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict a drug response. According to this method, if a gene that encodes a drug target is known (e.g., a Pin1 protein or Pin1 receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a Pin1 molecule or Pin1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a Pin1 molecule or Pin1 modulator, such as a modulator identified by one of the exemplary screening assays described herein.

4. Use of Pin1 Molecules as Surrogate Markers

The Pin1 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the Pin1 molecules of the invention may be detected, and may be correlated with one or more biological states in vivo. For example, the Pin1 molecules of the invention may serve as surrogate markers for one or more disorders or disease states or for conditions leading up to disease states.

As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the causation of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al: (2000) *J. Mass. Spectrom.* 35:258-264; and James (1994) *AIDS Treatment News Archive* 209.

The Pin1 marker molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a Pin1 marker) transcription or expression, the amplified marker may be in a quantity which is more readily detectable than the drug itself. Also, the marker may be more easily detected due to the nature of the marker itself; for example, using the methods described herein, anti-Pin1 antibodies may be employed in an immune-based detection system for a Pin1 protein marker, or Pin1-specific radiolabeled probes may be used to detect a Pin1 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229-238; Schentag (1999) *Am. J. Health-Syst. Pharm.* 56 Suppl. 3:S21-S24; and Nicolau (1999) *Am. J. Health-Syst. Pharm.* 56 Suppl. 3:S16-S20.

The Pin1 marker molecules of the invention are also useful as pharmacogenomic markers. As used herein, a "pharmacogenomic marker" is an objective biochemical marker which correlates with a specific clinical drug response or susceptibility in a subject (see, e.g. McLeod et al. (1999) *Eur. J. Cancer* 35(12):1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., Pin1 protein or RNA) for specific tumor markers in a subject, a drug or course of treatment may be selected that is optimized for the treatment of the specific tumor likely to be present in the subject. Similarly, the presence or absence of a specific sequence mutation in Pin1 DNA may correlate Pin1 drug response. The use of pharmacogenomic markers therefore permits the application of the most appropriate treatment for each subject without having to administer the therapy.

This invention is further illustrated by the following examples which should not be construed as limiting. The following examples show the use of Pin1 as a universal marker for abnormal cell growth, e.g., cancer and the involvement of Pin1 in tumorigenic pathways. The contents of all references, patents and published patent applications cited throughout this application, as well as the Figures, are incorporated herein by reference.

EXAMPLES

Example 1

Pin1 is a Breast Tumor Marker

To determine whether Pin1 is overexpressed in human tumor samples, we examined the levels of Pin1 in human breast cancer samples using immunoblotting and immunohistochemical analysis with Pin1 antibodies, as described previously (Lu et al. (1999) *Nature* 399:784-788). Immunocytochemistry of sections of human breast tumors showed that Pin1 is indeed overexpressed in human breast tumor cells. Pin1 was detected both in the cytoplasm and in the nucleus, as well as in condensed chromosomes and mitotic spindles. Infiltrating carcinoma cells were strongly positive for Pin1 staining, while surrounding normal connective tissue, blood vessels, adipose, and stromal cells were only weakly positive. To ensure that these signals represent Pin1, a control immunostaining was performed whereby the Pin1-specific antibodies were first specifically depleted by pre-incubation with glutathione beads containing GST-Pin1. This is depletion resulted in no detection of signal, demonstrating the specificity of the Pin1 antibodies used in the immunostaining. Furthermore, similar immunostaining in various breast tumor-derived cell lines, when compared with those in non-transformed mammary cell lines, showed significantly elevated expression of Pin1.

To confirm the immunostaining results and to establish a quantitative relationship between Pin1 expression and various known tumor markers, fresh normal and tumor breast tissues were ground in liquid nitrogen and lysates were directly subjected to immunoblotting analysis with various antibodies. Quantification of protein levels was carried out with "Imagequant" software, as described elsewhere (Lu et al. (1999) *Nature* 399:784-788). Using actin expression as a normalization control, Pin1 levels were compared as ratios of Pin1/actin expression. Using 10 non-cancerous breast tissue samples and 51 primary breast cancer tissue samples, we observed striking differences in levels of Pin1 protein between normal and neoplastic breast tissues. 71.4% of Grade II tumors and 89.5% of Grade III tumors overexpressed Pin1, wherein overexpression was defined as higher than mean plus three times standard deviation of the normal controls (FIGS. 1 and 2). Moreover, Pin1 levels positively correlated with the nuclear grade in invasive cancer, which is an important predictor of clinical aggressiveness of the tumors (Bloom-Richardson's classification; see, e.g., Bloom and Richardson, (1957) *Br. J. Cancer,* 11:359-377, and Bloom et al. (1962), *Brit. Med. J.* 5299:213). Taken together, these results indicate that Pin1 is over expressed in the majority of breast cancer samples, with the highest expression levels in high-grade tumors.

Pin1 levels were also compared to the levels of other known cancer markers (FIG. 3). It was observed that Pin1 levels did not correlate with either estrogen receptor or HER2/neu expression, but significantly correlated with cyclin D1 overexpression, as analyzed by the Kruskall-Wallis test (see, e.g., Glantz, S. A. (1997) *Primer of Biostatistics,* $4^{th}$ ed. McGraw Hill New York, pp 346-348). As expected, cyclin D1 was overexpressed in about 50% of the patent samples (24 out of 51). Importantly, Pin1 was overexpressed in 20 out of 24 cyclin D1 overexpressing tumors. Moreover, the level of Pin1 in these tumors was about twice as high (on average) as in cyclin D1 negative tumors. The correlation between Pin1 and cyclin D1 expression indicate that overexpression of Pin1 can be correlated with expression of endogenous cyclin D1.

In order to test for a causative correlation between Pin1 and cyclin D1 expression a breast tumor cell line (MCF-7) was stably transfected such that Pin1 is expressed under the control of the tetracycline-regulated promoter. Although expression of actin was not affected in these cells, induction of Pin1 expression resulted in about a 2.5 fold increase in cyclin D1 protein levels in two independent cell lines, while cyclin D1 levels remained stable in uninduced cells. These results demonstrate that up-regulation of Pin1 causes overexpression of endogenous cyclin D1 in human breast cancer cell lines.

Further immunoblotting and quantification experiments revealed that levels of Pin1 protein and beta-catenin protein can be correlated in breast cancer cells. Beta-catenin is a gene which is known to be involved in certain tumorigenic pathways (see, e.g., Polakis, (2000) *Genes Dev* 14:1837-51, Behrens, (2000) *N.Y. Acad Sci* 910:21-35; and Peifer and Polakis, (2000) *Science* 287:1606-9).

The expression of various other beta-catenin downstream target genes in Pin1-overexpressed MCF-7 cells was assessed using standard differential expression techniques (see, e.g., Ryo, et al (1998) *Nucleic Acids Res* 26:2586-92. The results are set forth in FIG. 4.

Example 2

Pin1 is a Colon Tumor Marker

To explore whether Pin1 is also overexpressed in colon tumors, we have examined the Pin1 levels in several human colon tumor samples using immunostaining and immunoblotting analyses (using the experimental methods set forth in Example 1). Pin1 was overexpressed in most samples examined, as compared with normal colon samples. These results indicate that Pin1 can act as marker for colon cancer.

Example 3

Pin1 as a Prostate Tumor Marker

To explore whether Pin1 is also overexpressed in prostate tumors, we have examined the Pin1 levels in several human prostate tumor samples using immunostaining and immunoblotting analyses (using the experimental methods set forth in Example 1). Pin1 was overexpressed in most samples examined, as compared with normal prostate samples. These results indicate that Pin1 can act as marker for prostate cancer.

Example 4

Pin1 is a Universal Marker of Proliferation

To further evaluate the potential of detecting Pin1 levels as a general marker for cell proliferation, the expression of Pin1 in an array of normal human tissues was assessed. A panel of 30 normal human tissues were stained with affinity-purified anti-Pin1 antibodies. Although very low levels of Pin1 were detected in non-epithelial cell types, such as different kinds of muscles, Pin1 was primarily detected at moderate levels in various types of epithelial cells, hemopoietic cells and at very high levels in germline cells of testis and ovary, especially in sperm. Specifically, it was observed that Pin1 expression in normal human tissues was associated with proliferative status. For example, cell proliferation primarily occurs at the base portion of clefts in colon and they stop proliferation when they move up along the cleft. In such areas, a gradient in the level of Pin1 signal was observed, e.g., Pin1 levels were much higher in the base portion than that in upper portion of clefts in colon. Similar-phenomena were also observed in other tissues, such as the transitional epithelial cells of bladder. With the exception of testis, Pin1 levels in normal human tissues are much lower than those observed in human breast or prostate tumor samples. These results further indicate that detection of Pin1 levels can be used as a diagnostic marker for abnormal proliferation in an array of human tissues and diseases.

Example 5

Pin1 is Involved in Tumorigenic Pathways

Figure 5:
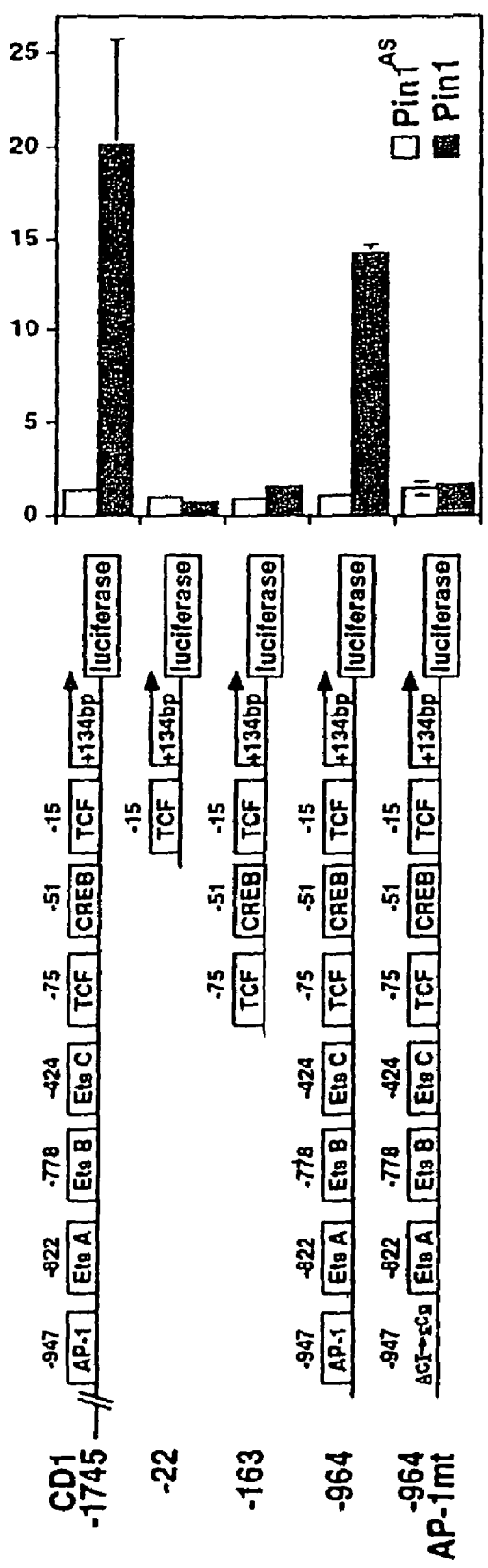
FIG. 5 depicts a representation of the cyclin D1 (CD1) pA3LUC basic reporter constructs (and AP-1 site mutant) which were used in Pin1 overexpressing Hela and MCF-7 cells (Pin1$^{AS}$ are the cells which overexpress the antisense construct). The activity of the reporter luciferase was expressed in relative activity in control vector transfected cells, which is defined as 1.0. Similar results were obtained in at least 3 different experiments. All results are expressed as $X_{mean} \pm SD$ of independent duplicate cultures.

The role of Pin1 in the modulation of various known tumorigenic pathways, such as those associated with beta-catenin and cyclin D1, was investigated in more detail. Although cyclin D1 overexpression is found in ~50% of breast cancer patients (Gillett, et al. (1994) Cancer Res 54:1812-1817, Bartkova, et al. (1994) Int J Cancer 57:353-361) gene amplification accounts for only 10% of these cases (Fantl, et al. (1993) Cancer Surv 18:77-94 (1993). Other mechanisms, such as up-regulation of gene transcription, must play a substantial role in the overexpression of cyclin D1. To determine whether Pin1 regulates transcription of cyclin D1, various cyclin D1 promoter-luciferase reporter constructs (full-length "−1745" and activated ras-responsive "−964" of FIG. 5, see, e.g., Motokura and Arnold (1993) Genes Chromosomes Cancer 7:89-95, and Albanese et al., (1995) JBC 270: 23589-23597) were transfected into HeLa and MCF-7 cells in order to measure the response to manipulating Pin1 function. The level of Pin1 in cells can be readily manipulated by expressing a sense or antisense Pin1 construct, respectively (see, e.g., Lu et al., (1996) Nature 380:544-547). FIG. 5 shows that both reporters were strongly transcribed in response to the expression of Pin1. Compared with the antisense construct, the Pin1 sense construct increased the activity of the cyclin D1 promoter by about 15 fold. These results indicate that Pin1 activates the cyclin D1 promoter and that the −964CD1 promoter fragment retains the complete responsiveness to Pin1. Similar promoter activation transfection experiments were conducted in inducible Pin1-expressing cells using the promoters for two genes associated with beta-catenin tumorigenic pathways (TCF-1 and c-myc) to drive luciferase expression. As with cyclin D1, Pin1 expression was able to induce these promoters as well.

FIG. 5 depicts how the −964CD1 promoter fragment (of the cyclin D1 gene) contains binding sites for various transcriptional factors including a CREB site, four TCF sites, three Ets sites and one AP-1 site. To determine which element in the promoter is necessary for the Pin1 responsiveness, two deletion constructs containing either 22 bp ("−22") or 163 bp ("−163") of the cyclin D1 promoter were created and subjected to similar transactivation assays. FIG. 5 shows that Pin1 did not have any significant transactivating effect either on the −22 or the −163 reporter. These results indicate that Pin1 does not affect the cyclin D1 promoter activity through the basic transcriptional machinery and suggest that the major sequences responsible for the Pin1 responsiveness may be the AP-1 site and/or Ets sites. To examine the importance of the AP-1 site, a mutant promoter, "−964 AP-1mt" which contains two base pair substitutions at the consensus AP-1 site was used (see, e.g., Albanese et al., supra). FIG. 5 shows that elimination of the AP-1 site completely abolished the ability of Pin1 to activate the cyclin D1 promoter. Interestingly, the same mutation has been shown also to completely abolish the Ras- or c-Jun-dependent activation of cyclin D1 expression. These results indicate that the AP-1 site is essential for activation of the cyclin D1 promoter by Pin1, as is by Ras- or c-Jun.

The AP-1 complex is composed of c-Jun and c-Fos proteins, with c-Jun being the most potent transactivator in the complex (see, e.g., Chiu et al (1989) Cell 59:979-986, Angel et al (1989) New Biol. 1:35-43, Abate, et al (1991) Mol Cell Biol 11:3624-3632. Various oncoproteins, including activated Ras, participate in a signaling cascade leading to phosphorylation of c-Jun on two S-P motifs (S63/73-P) to increase its transcriptional activity towards its target genes, including cyclin D1. In fact, Ras-mediated tumorigenesis depends on signaling pathways that act preferentially through cyclin D1 (Robles, et al. (1998) Genes Dev 12:2469-2474). Since Pin1 binds and regulates the function of phosphoproteins, it is possible that Pin1 activates the cyclin D1 promoter via modulating the activity of phosphorylated c-Jun. This possibility was tested by examining whether Pin1 binds to phosphorylated c-Jun. To manipulate phosphorylation of c-Jun on S63/73-P, we co-transfected c-Jun with the oncogenic Harvey-Ras (Ha-Ras or RasL61), the dominant-negative Ras (DN-Ras or RasN17) or the control vector, and then examined the ability of c-Jun to bind Pin1 by subjecting cell lysates to GST-Pin1 pulldown experiments (see, e.g., Yaffe, et al. (1997) Science 278:1957-1960, Shen, et al (1998) Genes Dev. 12:706-720, Lu, et al. (1999) Science 283, 1325-1328). Although there was no binding at all between GST and c-Jun, weak binding between GST-Pin1 and c-Jun was detected when only c-Jun was transfected. Furthermore, the binding was significantly increased by co-transfection with Ha-Ras, but not with DN-Ras. Since Ha-Ras is known to induce phosphorylation of c-Jun on S63/73-P, the binding may be mediated by phosphorylation on these residues. To test this possibility, we used a c-Jun mutant (c-JunS63/73A; contains double Ala substitutions at S63 and S73, see, e.g., Smeal, et al (1991) Nature 354:494-496). Although the mutant was expressed at much higher levels and did not display a significant mobility shift, as compared with wild type protein, much less of the mutant protein was precipitated by Pin1. These results indicate that although the mutant c-JunS63n73A may contain some other minor Pin1-binding site(s), phosphorylation of c-Jun on S63/

73-P is important for the Pin1 binding. Thus, Pin1 binds to c-Jun mainly via phosphorylated S63/73-P motifs.

Figure 6:
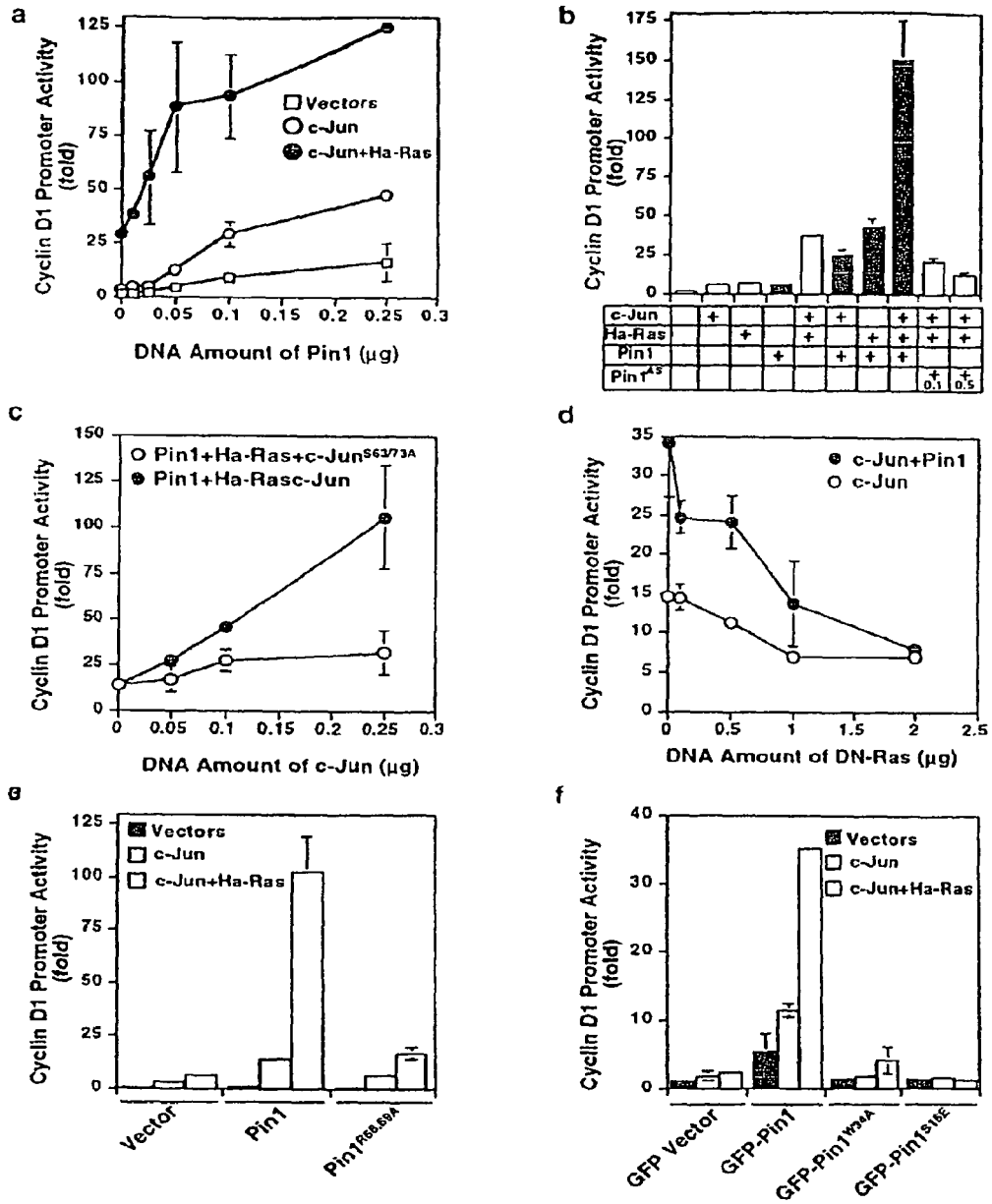
FIG. 6 depicts further cyclin D1 promoter activation experiments transfected Hela cells. Pin1 is shown to cooperate with Ha-Ras in enhancing the c-Jun activity towards the cyclin D1 promoter.

The ability of Pin1 to modulate the activity of c-Jun in activating the cyclin D1 promoter in presence or absence of activated Ras was next assessed. When Pin1 cDNA was co-transfected into HeLa cells with c-Jun, c-Jun and Ha-Ras or control vectors, Pin1 levels were slightly increased by co-transfection with c-Jun and further increased by co-transfection with c-Jun and Ha-Ras. These results indicate that Ha-Ras and c-Jun can increase the protein level of exogenously expressed Pin1. More importantly, although Pin1 did not affect levels of phosphorylated c-Jun in the presence or absence of Ha-Ras, Pin1 potently cooperated with c-Jun in activating the cyclin D1 promoter in a concentration-dependent manner (FIG. 6, panels "a" and "b"). The activity of the cyclin D1 promoter in cells co-transfected with Pin1 and c-Jun was 3-5 fold higher than that in cells transfected with either Pin1 or c-Jun alone. An even more dramatic potentiation of cyclin D1 reporter gene activity (by 5-10 fold) occurred if c-Jun was activated by Ha-Ras in the presence of Pin1. These results indicate that Pin1 and c-Jun cooperatively activate the cyclin D1 promoter and that this cooperation is further potentiated by oncogenic Ras.

The ability of Pin1 to activate the cyclin D1 promoter by modulating the activity of phosphorylated c-Jun was next assessed. To accomplish this, it was postulated that a mutation of the c-Jun phosphorylation sites would abolish the effect of Pin1 on the cyclin D1 promoter. The c-Jun S63n3 mutant was used to examine this possibility. As shown in FIG. 6, panel "c", Pin1 almost completely failed to cooperate with c-Jun$^{S63/73A}$ to induce the cyclin D1 promoter. These results indicate that phosphorylation of c-Jun on $S^{63/73}$ is essential for Pin1 to induce the cyclin D1 promoter. To further confirm this conclusion and to examine the importance of the Ras-dependent signaling in this regulation, we used DN-Ras to inhibit endogenous Ras function. DN-Ras not only inhibited the ability of c-Jun to activate the cyclin D1 promoter, but also potently inhibited the ability of Pin1 to enhance the activity of c-Jun in a concentration-dependent manner (FIG. 6, panel "d"). These results indicate a critical role of the Ras-dependent signaling for Pin1 to modulate c-Jun activity. These results together indicate that phosphorylation of c-Jun on $S^{63/73}$ induced by the Ras-dependent signaling pathway is essential for Pin1 to modulate the transcriptional activity of the cyclin D1 promoter.

To examine whether the activities of the WW domain and a PPIase domain are required for Pin1 to modulate the activity of c-Jun, similar experiments were carried out with Pin1 mutants, Pin1$^{R68,69A}$, Pin1$^{W34A}$ and Pin1$^{S16E}$, which contain mutations at the key residues either in the PPIase domain (R68, R69) or the WW domain (W34 or S16) and fail to isomerize pS/T-P bonds or to bind phosphoproteins. As shown in FIG. 6, panels "e" and "f", these Pin1 mutants neither increased the transcriptional activity of c-Jun towards the cyclin D1 promoter, nor potentiated the ability of Ha-Ras to activate c-Jun. These results indicate that both phosphoprotein-binding and phosphorylation-specific isomerase activities are required for Pin1 to modulate the activity of c-Jun.

To examine whether endogenous Pin1 is important for activation of the cyclin D1 promoter by c-Jun and H-Ras, we again transfected the expression vector which contains anti-sense Pin1 (Pin1$^{AS}$) which significantly reduces cellular Pin1 levels. When c-Jun and H-Ras were cotransfected with different concentrations of the Pin1$^{AS}$ construct, the cyclin D1 promoter activity was significantly decreased in a concentration-dependent manner (FIG. 6, panel "b"). Since depletion of Pin1 did not significantly affect levels of phosphorylated c-Jun, these results indicate that inhibiting endogenous Pin1 decreases the ability of phosphorylated c-Jun to activate the cyclin D1 promoter.

REFERENCES

Bailly et al. (1991) *Nature* 350:715-8
Blangy et al. (1995) *Cell* 83:1159-69
Bonnemann et al. (1996) *Curr Opinion Pediatr* 8:569-82. [a subsequent erratum appears in *Curr Opinion Pediatr* 1997 9:1961]
Bramblett et al. (1993) *Neuron* 10:1089-99
Clackson and Wells (1995) *Science* 267:383-6
Crenshaw et al. (1998) *EMBO J.* 17:1315-27
Davis et al. (1983) *Proc Natl Acad Sci USA* 80:2926-2930
Dolinski and Heitman (1997) Peptidyl-prolyl isomerases (PPIases). In: *Guidebook to Molecular Chaperones and Protein-Folding Catalysts*, M.-J. eds. Gething, Oxford University Press, pp. 359-369
Dolinski et al. (1997) *Proc. Natl. Acad. Sci. USA* 94:13093-131098
Ermekova et al. (1998) *Adv Exp Med Biol* 446:161-80
Hanes et al. (1989) *Yeast* 5:55-72
Hani et al. (1995) *Febs Lett* 365:198-202
Heald and McKeon (1990) *Cell* 61:579-89
Huibregtse et al. (1995) *Proc Natl Acad Sci USA* 92:2563-7 [a subsequent erratum appears in *Proc Natl Acad Sci USA* 92:5249]
Hunter (1998) *Cell* 92:141-143
Izumi and Maller (1993) *Mol Biol Cell* 4:1337-50
King et al. (1994) *Cell* 79:563-571
Kops et al. (1998) *J. Biol. Chem.* 273:31971-6
Lu (1999) *Prog. Cell Cycle Res.* (in press)
Lu et al. (1996) *Nature* 380:544-7
Lu and Hunter (1995a) *Cell* 81:413-424
Lu and Hunter (1995b) *Progress in Cell Cycle Research* 1:187-205
Lu et al. (1999) *Nature* (in press)
Lu et al. (1998) *Science* 283:1325-1328
Macias et al. (1996) *Nature* 382:646-9
Maleszka et al. (1996) *Proc Natl Acad Sci USA* 93:447-51
Marchal et al. (1998) *Mol Cell Biol* 18:314-321
Mayer and Baltimore (1993) *Trends Cell Biol* 3:8-13
Mayer et al. (1995) *Curr Biol* 5:296-305
Meyn (1997) *Oncology* 11:349-56 (see also discussion 356, 361 and 365)
Muschel et al. (1997) *Vitain Horm* 53:1-25
Nefsky and Beach (1996) *EMBO J.* 15:1301-12
Nigg (1995) *BioEssays* 17:471-480
Nurse (1994) *Cell* 79:547-550
Pawson and Schlessinger (1993) *Curr Biol* 3:434-442
Pawson and Scott (1997) *Science* 278:2075-80
Piccart and Di Leo (1997) *Semin Oncol* 24:S10-27-S10-33
Rahfeld et al. (1994) *FEBS Lett.* 343:65-69
Ranganathan et al. (1997) *Cell* 89:875-886
Rotin (1998) *Curr Top Microbiol Immunol* 228:115-33
Sabo et al. (1999) *J Biol Chem* 274:7952-7
Schlessinger et al. (1995) *Nature* 373:536-9
Schreiber (1991) *Science* 251:283-7
Schutkowski et al. (1998) *Biochemistry* 3 7:5566-75
Shen et al. (1997) *Proc. Natl. Acad. Sci. USA* 94:13618-13623
Shen et al. (1998) *Genes Dev.* 12:706-720
Staub et al. (1996) *EMBO J.* 15:2371-80
Stukenberg et al. (1997) *Curr Biol* 7:338-48
Sudol, M. (1996) *Prog Biophys Mol Biol* 65:113-32

Uchida et al. (1999) *FEBS Lett.* 446:278-82
Winder (1997) *J Muscle Res Cell Motil* 18:617-29
Yaffe et al (1997) *Science* 278:1957-1960
Kuang et al. (1997) *Science* 278:1957-1960.
Yoshida and Ihara (1993) *J Neurochern* 61:1183-6
Young et al. (1994) *Protein Sci* 3:717-29
Zhou et al. (1995) *Nature* 373:536-9

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining the amount of abnormal cell growth in a mammal by assessing the level of Pin1 in a test sample from the mammal, comprising the steps of:
   contacting the test sample with an antibody having specificity for Pin1 under conditions suitable for binding of the antibody to Pin1, thereby resulting in the formation of a complex between the antibody and Pin1, and
   comparing the amount of the complex in the test sample with an amount of a complex in a control sample,
   wherein an elevation in the amount of the complex in the test sample compared to the control sample is indicative of the amount of abnormal cell growth.

2. The method of claim 1, wherein the abnormal cell growth is cancer.

3. The method of claim 2, wherein the cancer is a malignant cancer.

4. The method of claim 2, wherein the cancer is breast, prostate, or colon cancer.

5. The method of claim 1, wherein the antibody is a monoclonal antibody.

6. The method of claim 1, wherein the antibody is a polyclonal antibody.

7. The method of claim 1, wherein the complex is detected by incubating the complex with a second antibody specific for the complex, said second antibody comprising a detectable label.

8. The method of claim 7, wherein the detectable label is selected from the group consisting of a radioactive, enzymatic, biotinylated, and fluorescent label.

9. The method of claim 1, wherein determining the amount of abnormal cell growth comprises determining the aggressiveness or metastasis of the abnormal cell growth.

10. The method of claim 1, further comprising determining a ratio of the amount of Pin1 bound to a Pin1-specific antibody in the test sample to an amount of a non-Pin1 cellular protein in the test sample, wherein the non-Pin1 cellular protein is selected from the group consisting of actin and tubulin.

* * * * *